US011209433B2

(12) United States Patent
Campbell et al.

(10) Patent No.: US 11,209,433 B2
(45) Date of Patent: Dec. 28, 2021

(54) METHODS AND KITS FOR THE DIAGNOSIS OF INFLUENZA

(71) Applicant: Becton, Dickinson and Company, Franklin Lakes, NJ (US)

(72) Inventors: Robert Campbell, Bullock, NC (US); Kevin G. Dolan, Holly Springs, NC (US); Eric Fallows, Apex, NC (US); Randal A. Hoke, Cary, NC (US); Ross Jacobson, Hillsborough, NC (US); J. Bruce Pitner, Durham, NC (US); Glenn P. Vonk, Fuquay Varina, NC (US); Rajashaker Kache, Cary, NC (US); Upma Gulati, Cary, NC (US); Herman D. Himel, IV, Cary, NC (US); Rosemary B. Evans-Storms, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/384,020

(22) Filed: Apr. 15, 2019

(65) Prior Publication Data

US 2019/0339272 A1 Nov. 7, 2019

Related U.S. Application Data

(62) Division of application No. 14/781,008, filed as application No. PCT/US2014/032567 on Apr. 1, 2014, now Pat. No. 10,317,404.

(60) Provisional application No. 61/807,185, filed on Apr. 1, 2013.

(51) Int. Cl.
*C07H 15/203* (2006.01)
*G01N 33/569* (2006.01)

(52) U.S. Cl.
CPC ..... *G01N 33/56983* (2013.01); *C07H 15/203* (2013.01); *G01N 2333/11* (2013.01); *G01N 2333/924* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 4,590,169 | A | 5/1986 | Cragle |
| 4,810,631 | A | 3/1989 | Perlman |
| 4,835,099 | A | 5/1989 | Mize |
| 4,904,583 | A | 2/1990 | Mapes |
| 5,017,473 | A | 5/1991 | Wagner |
| 5,314,801 | A | 5/1994 | Nycz |
| 5,457,027 | A | 10/1995 | Nadeau |
| 5,470,723 | A | 11/1995 | Walker |
| 5,518,884 | A | 5/1996 | Spears |
| 5,561,044 | A | 10/1996 | Walker |
| 5,639,428 | A | 6/1997 | Cottingham |
| 5,736,365 | A | 4/1998 | Walker |
| 5,998,221 | A | 12/1999 | Malick |
| 6,194,220 | B1 | 2/2001 | Malick |
| 6,267,722 | B1 | 7/2001 | Anderson |
| 6,303,764 | B1 | 10/2001 | Srivastava |
| 6,394,952 | B1 | 5/2002 | Anderson |
| 6,420,552 | B1 | 7/2002 | Srivastava |
| 6,680,054 | B1 | 1/2004 | Reece |
| 6,867,051 | B1 | 3/2005 | Anderson |
| 7,291,488 | B2 | 11/2007 | Wolfe |
| 7,642,060 | B2 | 1/2010 | Nagar |
| 7,893,272 | B2 | 2/2011 | Li |
| 7,947,820 | B2 | 5/2011 | Wolfe |
| 8,007,999 | B2 | 8/2011 | Holmes et al. |
| 8,163,237 | B2 | 4/2012 | Crawford |
| 8,221,976 | B2 | 7/2012 | Wolfe |
| 8,298,757 | B2 | 10/2012 | Takahashi et al. |
| 2004/0086849 | A1 | 5/2004 | Shimasaki et al. |
| 2007/0264629 | A1 | 11/2007 | Holmes et al. |
| 2009/0280504 | A1 * | 11/2009 | Lu .................... G01N 33/56983 435/7.1 |
| 2011/0189655 | A1 | 8/2011 | Li |

FOREIGN PATENT DOCUMENTS

| | | | |
|---|---|---|---|
| CN | 101437550 | A | 5/2009 |
| EA | 14533 | B1 | 12/2010 |
| EP | 0369657 | A2 | 5/1990 |
| EP | 2 063 270 | | 11/2012 |
| JP | 2002541858 | A | 12/2002 |
| JP | 2008-014751 | | 1/2008 |
| WO | WO 1998/013372 | | 4/1998 |
| WO | WO 1999/031280 | | 6/1999 |
| WO | WO 2007/053487 | | 5/2007 |
| WO | WO 2007/134166 | A2 | 11/2007 |
| WO | WO 2009/014787 | | 1/2009 |
| WO | WO 2010/139047 | | 12/2010 |
| WO | WO 2014/165536 | | 10/2014 |

OTHER PUBLICATIONS

Golightly, et al., Surface-Enhanced Raman Spectroscopy and Homeland Security: A Perfect Match?, ACS Nano, 209 3(1):2859-2869 (2009).

Mize et al., Dual Enzyme Cascade—An Amplified Method for the Detection of Alkaline Phosphate, Analytical Biochemistry, 179:229-235 (1989).

Peci et al., Community-acquired respiratory viruses and co-infection among patients of Ontario sentinel practices, Apr. 2009 to Feb. 2010, Influenza and Other Respiratory Viruses 7(4):559-566 (2013).

Peters et al., 2013, Evaluation of the limit of detection of the BD Veritor system flue A+B test and two rapid influenza detection tests for influenza virus, Diagnostic Microbiology and Infectious Disease, 75:200-202.

(Continued)

*Primary Examiner* — Benjamin P Blumel
(74) *Attorney, Agent, or Firm* — Knobbe Martens Olson & Bear LLP

(57) ABSTRACT

Some embodiments provided herein relate to combined assays. In some embodiments, an assay for identifying influenza type A or influenza type B is combined with an assay for determining the sensitivity of an influenza neuraminidase to an antiviral drug.

42 Claims, 14 Drawing Sheets

(56) References Cited

OTHER PUBLICATIONS

Sheu, et al., Surveillance for Neuraminidase Inhibitor Resistance among Human Influenza A and B Viruses Circulating Worldwide from 2004 to 2008, Antimicrobial Agents and Chemotherapy, 52(9)9:3284-3292 (2008).
Sidwell et al., In vitro and in vivo assay systems for study of influenza virus inhibitors, Antiviral Res. (2000) 48:1-16.
Shimasaki et al., Rapid Diagnostics: the detection of neuraminidase activity as a technology for high-specificity targets, Phil. Trans. R. Soc. Lond. B, 356:1925-1931 (2001).
Wang et al., Influenza and Bacterial Pathogen Coinfections in the $20^{th}$ Century, Interdisciplinary Perspectives on Infectious Diseases, vol. 2011 Article ID 146376 (2011).
International Search Report and Written Opinion issued in PCT/US2014/032567 dated Sep. 8, 2014.
Yang et al., Regioselective intramolecular oxidation of phenols and anisoles by dioxiranes generated in situ. The Journal of organic chemistry, (2000).65(13), 4179-4184.
Australian Examination Report dated Jul. 2, 2019 for Application No. 2014248225, filed Sep. 30, 2015.
Japanese Office Action dated Dec. 7, 2020 for Application No. 2019-169472, filed Sep. 18, 2019.
Canadian Office Action dated Apr. 1, 2021 for Application No. 2,908,028, filed Sep. 24, 2015.
Chinese Office Action and Search Report dated May 18, 2021 for Application No. 201810491986.5, filed May 22, 2018.
India Office Action and Search Report dated Mar. 5, 2020 for Application No. 8985/DELNP/2015, filed Sep. 30, 2015.
Korean Office Action dated May 11, 2020 for Application No. 10-2015-7031383, filed Oct. 30, 2015.

* cited by examiner

Chemical Formula: $C_{21}H_{26}F_3NO_{10}$
Exact Mass: 509.15
Molecular Weight: 509.43

Chemical Formula: $C_{10}H_9F_3O_2$
Exact Mass: 218.06
Molecular Weight: 218.17

METHODS AND KITS FOR THE DIAGNOSIS OF INFLUENZA

CROSS-REFERENCE TO RELATED APPLICATIONS

This application is a division of U.S. application Ser. No. 14/781,008 filed Sep. 28, 2015 which is the U.S. National Phase of Application No. PCT/US2014/032567 entitled “METHODS AND KITS FOR THE DIAGNOSIS OF INFLUENZA” filed Apr. 1, 2014 and published in English on Oct. 9, 2014 as WO2014/165536 which claims the benefit of U.S. Provisional Application No. 61/807,185 filed Apr. 1, 2013 entitled “Point Of Care (POC) Influenza Antiviral Susceptibility Test” each of which is incorporated herein by reference in its entirety.

STATEMENT REGARDING FEDERALLY SPONSORED R&D

This invention was made with government support under HHSO100201300008C awarded by the Department of Health and Human Services. The government has certain rights in the invention.

FIELD OF THE INVENTION

Some embodiments provided herein relate to methods, compositions, devices and systems for point of care influenza tests. Some embodiments relate to combined assays. In some embodiments, an assay for identifying influenza type A or influenza type B is combined with an assay for determining the sensitivity of an influenza neuraminidase to an antiviral drug.

BACKGROUND OF THE INVENTION

Influenza is a constant and serious threat to public health. Each year, influenza associated illness leads to approximately 200,000 hospitalizations and 36,000 deaths in the United States. From a national impact perspective, the total economic costs in 2010 from influenza were estimated at $29 Billion. Antiviral therapy for influenza is effective, when given as a treatment or given for prophylaxis in a timely manner. Several studies conclude neuraminidase drugs reduce the duration of symptoms. Tamiflu and Relenza are both 80% effective in prophylaxis against seasonal flu. When treating patients with influenza, it is recommended that the patient start therapy within 48 hours of symptoms and smaller delays are better. Prompt diagnosis and initiation of the antiviral therapy leads to the best patient outcome.

Based on widespread resistance to the M2 channel blockers, it is not unreasonable to speculate that widespread use of neuraminidase inhibitors may ultimately lead to an emergence of their resistance in seasonal or pandemic influenza virus. A number of neuraminidase inhibitor resistant mutants have been identified during clinical studies. In a three-year period of surveillance, eight virus variants with a >10-fold decrease in susceptibility to oseltamivir were isolated. These findings should cause pause when considering the mass distribution of neuraminidase inhibitor-based drugs for the management of seasonal flu. In 2010 the WHO held the first global consultation on antiviral resistance in Hong Kong, following the emergence of transmissible oseltamivir-resistant influenza virus during the 2007-2008 winter season and detections of oseltamivir resistance in HSN1 and pandemic influenza H1N1 (2009). A key outcome from this consultation was the requirement for formal state reporting of antiviral resistance to influenza, either in clinical settings or as part of national surveillance. Moreover, some antivirals like oseltamivir cause adverse events making it important to only prescribe when required. Coverage for the various antiviral drugs can vary with provider and have different costs to the patient. The physician has a responsibility to only prescribe what is needed. While cost is secondary to effectiveness, if a patient can get by with a less expensive drug, the physician has an obligation to make the patient aware of the option. Accordingly, there is an unmet need for point of care tests that can provide diagnosis of a specific strain to avoid adverse events, slow down the evolution of drug resistance, and create a savings to the patient and the U.S. healthcare system.

SUMMARY OF THE INVENTION

Some embodiments of the methods, kits, systems, and compositions provided herein include a method for detecting an influenza virus comprising: (a) contacting a sample with an immunoassay buffer adapted for an immunoassay for detecting an influenza virus type A or an influenza virus type B, thereby obtaining an immunoassay test sample; (b) contacting a first portion of the immunoassay test sample to a test comprising an immunoassay for detecting an influenza type A or type B, thereby detecting the presence or absence of influenza type A or type B in the sample; (c) contacting a second portion of the immunoassay test sample with a matrix comprising a neuraminidase assay buffer, thereby obtaining a neuraminidase test sample; and (d) contacting the neuraminidase test sample with a neuraminidase assay, thereby detecting the presence of a neuraminidase in the sample. In some embodiment, the immunoassay buffer is incompatible with an assay for neuraminidase activity. In some embodiment, the immunoassay buffer inhibits neuraminidase activity. In some embodiment, steps (c) and (d) are performed in the same vessel.

Some embodiments provided herein include a method for detecting an influenza virus comprising: (a) contacting a sample with a neuraminidase assay buffer adapted for an neuraminidase assay, thereby obtaining a neuraminidase test sample; (b) contacting a first portion of the neuraminidase test sample to a test comprising an immunoassay for detecting an influenza type A or type B, wherein the neuraminidase test sample contacts a matrix comprising immunoassay buffer, thereby obtaining an immunoassay test sample and detecting the presence or absence of influenza type A or type B in the sample; and (c) contacting a second portion of the neuraminidase test sample with a neuraminidase assay, thereby detecting the presence of a neuraminidase in the sample. In some embodiment, the neuraminidase assay buffer is incompatible with an immunoassay for detecting an influenza type A or type B. In some embodiment, the neuraminidase assay buffer inhibits specific binding of an antibody to an antigen selected from the group consisting of influenza type A and influenza type B. In some embodiment, the matrix comprises lyophilized or dried down immunoassay buffer. In some embodiment, step (c) is performed in a vessel comprising a plurality of chambers.

In some embodiments of the methods for detecting an influenza virus the vessel comprises a plurality of chambers. In some embodiments, the vessel comprises a chamber comprising the matrix, and a chamber comprising reagents for the neuraminidase assay. In some embodiments, the matrix comprises a cross-linked polysaccharide. In some embodiments, the matrix is selected from the group consisting of sephadex and sepharose.

In some embodiments, the immunoassay test sample and the neuraminidase test sample are moved in the vessel by one or more forces selected from gravity, capillary action, and diffusion.

In some embodiments, the vessel comprises a cartridge. In some embodiments, the vessel comprises a multiwell cartridge adapted to be read using a photomultiplier. In some embodiments, the photomultiplier is selected from the group consisting of a photomultiplier tube and micro-photomultiplier tube. In some embodiments, the photomultiplier is portable. In some embodiments, the photomultiplier is in a portable reader suitable for a primary care physician's office. In some embodiments, the photomultiplier tube surface is round and has a diameter of about 6 mm to 9 mm, or the micro-photomultiplier tube is rectangular and has a dimension of about 1 mm to 3 mm.

In some embodiments, the neuraminidase assay comprises determining the sensitivity of a neuraminidase to a test compound. In some embodiments, the neuraminidase assay comprises: (a) obtaining an inhibition value ratio, wherein the ratio comprises the level of neuraminidase activity in the presence of a test compound compared to the level of neuraminidase activity in the absence of the test compound; and (b) comparing the inhibition value ratio to an inhibition threshold, thereby determining the sensitivity of the neuraminidase activity to the test compound. In some embodiments, the inhibition threshold is determined by the detection of a type A or a type B virus. In some embodiments, a first inhibition threshold is used if type A virus is detected, and a second inhibition threshold is used if type B virus is detected. In some embodiments, the first threshold is lower than the second threshold. In some embodiments, the inhibition threshold is determined by the test compound.

Some embodiments also include selecting the test compound for treating the influenza.

In some embodiments, the neuraminidase assay comprises a dual enzyme assay comprising a signaling enzyme. In some embodiments, neuraminidase activity produces a substrate for the signaling enzyme. In some embodiments, the neuraminidase assay comprises a conjugate of a N-acetylneuraminic acid and luciferin or a derivative thereof. In some embodiments, neuraminidase activity produces an inhibitor for the signaling enzyme. In some embodiments, the neuraminidase assay comprises a conjugate of a N-acetylneuraminic acid and a trifluoromethylketone or a derivative thereof. In some embodiments, the signaling enzyme comprises luciferase. In some embodiments, the immunoassay buffer inhibits luciferase activity. In some embodiments, the level of neuraminidase activity is measured using a photomultiplier tube.

In some embodiments, the test compound is an antiviral drug. In some embodiments, the test compound is an antiviral drug selected from the group consisting of Oseltamivir, Zanamivir, Lanamivir, and Peramivir.

In some embodiments, the immunoassay comprises a sandwich assay.

In some embodiments, the sample is obtained from a subject. In some embodiments, the subject is suspected of having influenza. In some embodiments, the subject is human.

Some embodiments provided herein include a method for selecting a treatment for an influenza virus comprising: (a) contacting a sample with an immunoassay buffer adapted for an immunoassay for detecting an influenza virus type A or an influenza virus type B, thereby obtaining an immunoassay test sample; (b) contacting a first portion of the immunoassay test sample to a test comprising an immunoassay for detecting an influenza type A or type B, thereby detecting the presence or absence of influenza type A or type B in the sample; (c) contacting a second portion of the immunoassay test sample with a matrix comprising a neuraminidase assay buffer, thereby obtaining a neuraminidase test sample; (d) contacting the neuraminidase test sample with a neuraminidase assay, thereby determining the sensitivity of a neuraminidase of the neuraminidase test sample to a test compound, the determining comprising: (i) obtaining an inhibition value ratio, wherein the ratio comprises the level of neuraminidase activity in the presence of one or more test compounds compared to the level of neuraminidase activity in the absence of the one or more test compounds, and (ii) comparing the inhibition value ratio to an inhibition threshold, thereby determining the sensitivity of the neuraminidase activity to the test compound; and (e) selecting a test compound from the one or more test compounds that was determined to inhibit neuraminidase activity. In some embodiments, the immunoassay buffer is incompatible with an assay for neuraminidase activity. In some embodiments, the immunoassay buffer inhibits neuraminidase activity. In some embodiments, steps (c) and (d) are performed in the same vessel.

Some embodiments provided herein include a method for selecting a treatment for an influenza virus comprising: (a) contacting a sample with a neuraminidase assay buffer adapted for an neuraminidase assay, thereby obtaining a neuraminidase test sample; (b) contacting a first portion of the neuraminidase test sample to a test comprising an immunoassay for detecting an influenza type A or type B, wherein the neuraminidase test sample contacts a matrix comprising immunoassay buffer, thereby obtaining an immunoassay test sample and detecting the presence or absence of influenza type A or type B in the sample; and (c) contacting a second portion of the neuraminidase test sample with a neuraminidase assay, thereby determining the sensitivity of a neuraminidase of the neuraminidase test sample to a test compound, the determining comprising: (i) obtaining an inhibition value ratio, wherein the ratio comprises the level of neuraminidase activity in the presence of one or more test compounds compared to the level of neuraminidase activity in the absence of the one or more test compounds, and (ii) comparing the inhibition value ratio to an inhibition threshold, thereby determining the sensitivity of the neuraminidase activity to the test compound; and (e) selecting a test compound from the one or more test compounds that was determined to inhibit neuraminidase activity. In some embodiments, the matrix comprises lyophilized or otherwise dried down immunoassay buffer. In some embodiments, step (c) is performed in the same vessel. In some embodiments, step (c) is performed in a vessel comprising a plurality of chambers.

In some embodiments of the methods for selecting a treatment for an influenza virus, the inhibition threshold is determined by the detection of the type A or a type B virus. In some embodiments, a first inhibition threshold is used if type A virus is detected, and a second inhibition threshold is used if type B virus is detected. In some embodiments, the first threshold is lower than the second threshold.

In some embodiments, the vessel comprises a multiwell strip or cartridge adapted to be read using a photomultiplier tube or micro-photomultiplier tube. In some embodiments, the photomultiplier tube micro-photomultiplier tube is portable. In some embodiments, the photomultiplier tube is in a portable reader suitable for a primary care physician's office. In some embodiments, the photomultiplier tube surface is round and has a diameter of about 6 mm to 9 mm, or the micro-photomultiplier tube is rectangular and has a dimension of about 1 mm to 3 mm.

Some methods also include selecting the test compound for treating the influenza.

In some embodiments, the neuraminidase assay comprises a dual enzyme assay comprising a signaling enzyme. In some embodiments, neuraminidase activity produces a substrate for the signaling enzyme. In some embodiments, the neuraminidase assay comprises a conjugate of a N-acetylneuraminic acid and luciferin or a derivative thereof. In some embodiments, neuraminidase activity produces an inhibitor for the signaling enzyme. In some embodiments, the neuraminidase assay comprises a conjugate of a N-acetylneuraminic acid and a trifluoromethylketone or a derivative thereof. In some embodiments, the signaling enzyme comprises luciferase.

In some embodiments, the level of neuraminidase activity is measured using a photomultiplier tube.

In some embodiments, the test compound is an antiviral drug. In some embodiments, the test compound is an antiviral drug selected from the group consisting of Oseltamivir, Zanamivir, Lanamivir, and Peramivir.

In some embodiments, the immunoassay comprises a sandwich assay.

In some embodiments, the sample is obtained from a subject. In some embodiments, the subject is suspected of having influenza. In some embodiments, the subject is human. In some embodiments, the subject sample was obtained from a subject, and the subject is advised to take the selected test compound to treat influenza. In some embodiments, the subject sample was obtained from a subject, and the subject is provided with the selected test compound to treat influenza.

Some embodiments include a diagnostic system for detecting influenza virus comprising: a cartridge for determining neuraminidase activity in a sample, wherein the cartridge is configured to process a sample comprising an incompatible buffer for the determination to a sample comprising a compatible buffer for the determination; a test for detecting influenza type A or type B in the sample, wherein the test is configured to process a sample comprising an incompatible buffer for the detection to a sample comprising a compatible buffer for the detection; a first detector configured to measure a signal from the test; and a second detector configured to measure a signal from the cartridge.

In some embodiments, the cartridge comprises a matrix chamber comprising a cartridge matrix comprising the compatible buffer for the determination, and a reagent chamber comprising reagents for the neuraminidase activity determination. In some embodiments, the cartridge matrix comprises a cross-linked polysaccharide. In some embodiments, the cartridge matrix is selected from the group consisting of sephadex and sepharose.

In some embodiments, the matrix chamber and cartridge chamber are in fluid communication such that a sample applied to the matrix chamber flows from the matrix chamber to the reagent chamber. In some embodiments, the sample flows in the cartridge by one or more forces selected from gravity, capillary action, and diffusion.

In some embodiments, the cartridge comprises a multi-well cartridge adapted to be read using a photomultiplier tube or micro-photomultiplier tube.

In some embodiments, the test comprises an immunoassay. In some embodiments, the immunoassay is a sandwich assay In some embodiments, the test comprises a matrix comprising the compatible buffer for the detection. In some embodiments, the matrix comprises nitrocellulose. In some embodiments, the compatible buffer for the detection is lyophilized or dried down.

In some embodiments, the first detector comprises a luminometer. In some embodiments, the first detector comprises a reflectance reader. In some embodiments, the second detector comprises a photomultiplier tube or micro-photomultiplier tube. In some embodiments, a device comprises the first and second detectors. In some embodiments, the first and second detectors are the same.

In some embodiments, the device is portable. In some embodiments, the device is handheld.

Some embodiments include a kit for detecting influenza virus comprising: a cartridge for determining neuraminidase activity in a sample, wherein the cartridge is configured to process a sample comprising an incompatible buffer for the determination to a sample comprising a compatible buffer for the determination; and a test for detecting influenza type A or type B in the sample, wherein the test is configured to process a sample comprising an incompatible buffer for the detection to a sample comprising a compatible buffer for the detection. Some embodiments include a first detector configured to measure a signal from the test; and a second detector configured to measure a signal from the cartridge. Some embodiments include reagents for a neuraminidase activity assay. In some embodiments, the neuraminidase activity assay reagents are selected from the group consisting of luciferase, a conjugate of a N-acetylneuraminic acid and luciferin or a derivative thereof, a N-acetylneuraminic acid and a trifluoromethylketone or a derivative thereof, and an antiviral drug. In some embodiments, the antiviral drug is selected from the group consisting of Oseltamivir, Zanamivir, Lanamivir, and Peramivir. Some embodiments include reagents for an immunoassay. In some embodiments, the immunoassay reagents are selected from the group consisting of an antibody specific to an influenza type A antigen, and an antibody specific to an influenza type B antigen.

Some embodiments include a masked inhibitor compound for use in a dual enzyme influenza neuraminidase sensitivity assay having the structure of Formula (I):

(I)

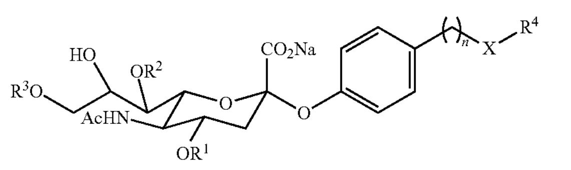

wherein: $R^1$, $R^2$ and $R^3$ are each independently hydrogen or $C_{1-5}$ alkyl; n is 0, 1, 2 or 3; $R^4$ is $—(CH_2)_mC(=O)CF_3$; m is 0 or 1; X is $—S(O)_z—$ or $—CH(R^5)—$; $R^5$ is $—S(O)_zCH_3$; and z is 0, 1 or 2.

In some embodiments, the compound of Formula (I) is selected from the group consisting of:

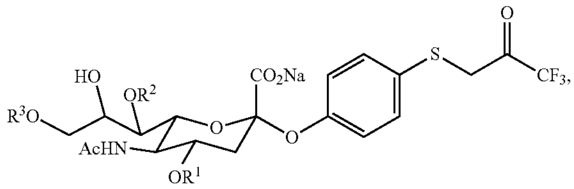,

-continued

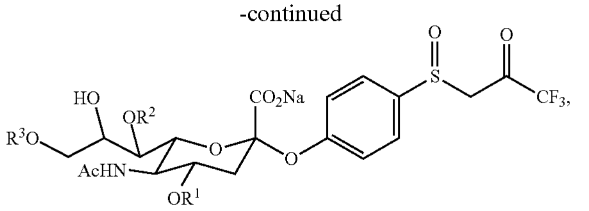

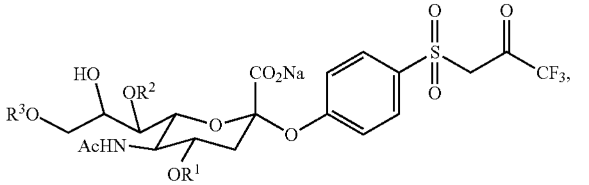

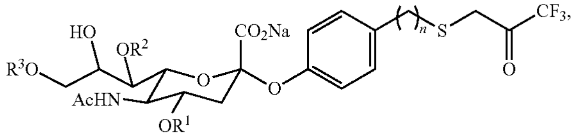

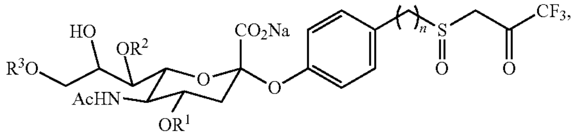

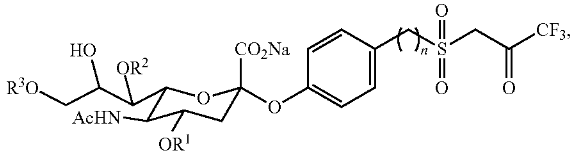

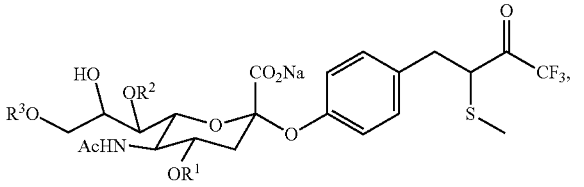

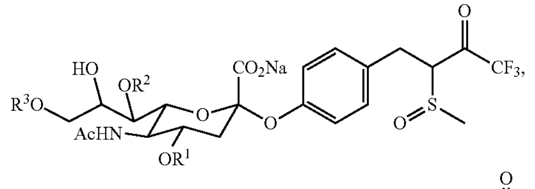

and

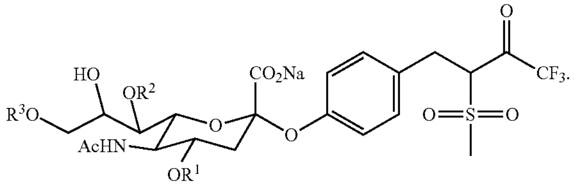

DETAILED DESCRIPTION

Figure 1:
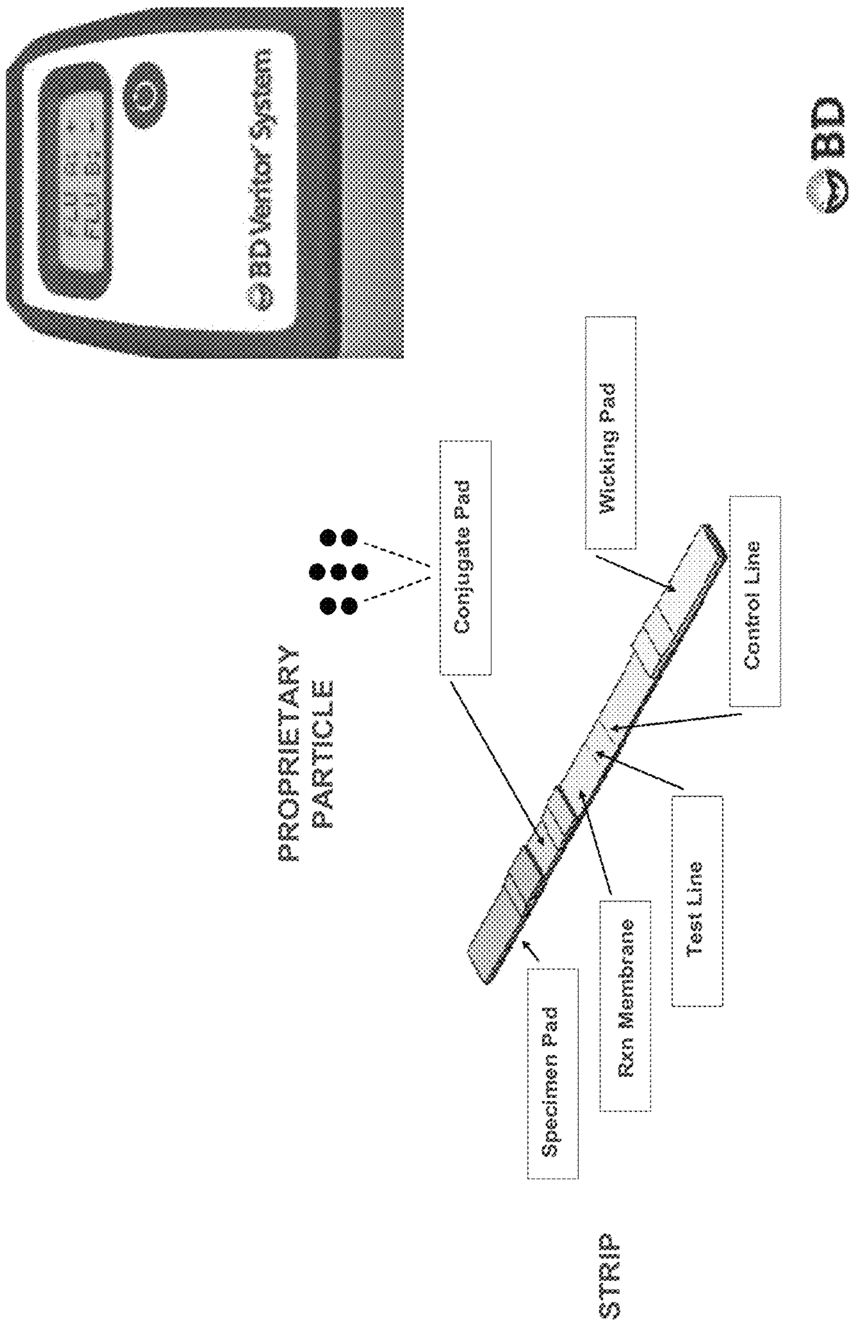
FIG. 1 depicts an embodiment of an immunoassay test strip and reader for the Veritor System (Becton Dickinson.).

Some embodiments of the methods, compositions, kits, devices and systems provided herein include a point of care (POC) combination diagnostic capable of identifying Influenza A or B and guiding antiviral therapy. In some embodiments, a portable platform can be operable by medical personnel with limited laboratory skills. Some embodiments include a lateral flow technology for influenza detection with an assay for detecting antiviral resistance strains, direct from clinical isolates without any cell culture amplification.

Some embodiments of the methods and compositions provided herein include combination assays in which a sample is assayed for (1) identification of type A or type B influenza virus in the sample; and (2) sensitivity of the influenza virus neuraminidase to one or more antiviral drugs. Typically, a sample prepared for use in an immunoassay to identify a type A or a type B influenza virus is incompatible for use in an assay relating to virus neuraminidase activity. For example, a lysis buffer for use in an immunoassay may inhibit a neuraminidase activity assay. Embodiments of the methods and compositions provided herein include methods for using an immunoassay and a neuraminidase activity assay from a single sample in an initial buffer compatible with one of the assays. Some such embodiments provide rapid testing for influenza type and provide guidance for selecting an antiviral drug for treatment.

In addition, some embodiments provided herein greatly enhance the sensitivity of such assays. In some embodiments, an assay to identify the type of influenza in a sample advantageously informs the analysis of an assay to determine the sensitivity or resistance of an influenza neuraminidase to an antiviral drug. In some embodiments, a threshold inhibition value for a type A or a type B virus for a particular antiviral drug can be selected and can be used to determine whether a neuraminidase is sensitive or resistant to the antiviral drug.

Some embodiments provided herein include the integration of two assays for a greater benefit to the patient. Embodiments provided herein dramatically improve the sensitivity of an influenza identification assay. In addition, both assays can be performed with the same volume of specimen. In some embodiments, an initial immunoassay and extraction buffer useful with such an assay can go unchanged, avoiding the need to submit an already commercialized assay to a new clinical trial. In some embodiments, a specimen in a buffer suitable for a flu immunoassay to determine flu type can be converted to a specimen in a buffer suitable for a neuraminidase drug sensitivity assay. In some embodiments, a specimen in a buffer suitable for a neuraminidase drug sensitivity assay can be converted to a specimen in a buffer suitable for a flu immunoassay to determine flu type. In some of the foregoing embodiments, conversion can occur in a time period suitable for a point of care diagnostic test. In some embodiments, time period suitable for a point of care diagnostic test can include less than about 1 day, less than about 12 hours, less than about 6 hours, less than about 3 hours, less than about 1 hour, less than about 30 minutes, less than about 10 minutes, less than about 5 minutes, less than about 1 minute, and a period between any of the foregoing times.

Some embodiments of the methods and compositions provided herein can provide specific drug inhibition values in neuraminidase drug sensitivity assays that are remarkably lower than other prior assays. Such drug inhibition values allow a determination whether an influenza variant is drug resistant or drug sensitive. The improved sensitivity results in fewer erroneous results, where flu is identified as not being drug resistant when in fact it is.

Some embodiments include a flu identification component which includes a lateral flow immunoassay that utilizes a nanoparticle for detection, focuses on the presence of influenza nucleocapsid and has a reader capable of forwarding automatically the flu typing result (Flu A vs. Flu B) to reader module and thereby applying the most appropriate drug inhibition value to use in a subsequent test for distinguishing drug sensitivity from drug resistance. In some embodiments, the flu identification component provides the information regarding flu type to the drug sensitivity component without further human intervention.

Some embodiments include a dual or two-enzyme assay for drug susceptibility testing that leverages the activity of the influenza neuraminidase, and whereby the first enzyme (neuraminidase) acts on a first substrate which releases a second substrate that can be acted upon by a second enzyme involved in signal generation.

Multiple versions of a two-enzyme assay or dual enzyme assay are compatible with the embodiments disclosed herein. In some embodiments, the result of the first enzyme-substrate reaction can be a substrate that is acted upon by a second enzyme, where signal increases with more influenza antigen and decreases when an effective influenza antiviral is present. In some embodiments, the result of the first enzyme-substrate reaction can be a compound which functions as an inhibitor of the second enzyme reaction. In some embodiments, the first substrate is a masked inhibitor, that is, it is a precursor to an inhibitor. In some embodiments, signal goes down when more influenza antigen is present and signal goes up when an effective influenza antiviral is present. Some embodiments of the methods and compositions provided herein include dual enzyme assays that can deliver good sensitivity for the influenza neuraminidase and the sensitivity can range from 10 picomolar to 100 fentamolar.

Currently the most effective antivirals for influenza treatment target the neuraminidase. The two mainstay neuraminidase inhibitor drugs are zanamivir (RELENZA™) and oseltamivir (TAMIFLU™). Flu strains resistant to these drugs can go undetected during the initial physician visit, causing additional stress to the patient which could be avoided with a POC antiviral drug resistance test. In the U.S. and other industrialized countries, antiviral susceptibility testing is primarily performed by government labs, far away from the patient and long after their visit with a primary care physician, as a component of surveillance. Until recently it was not conceivable that such tests could be performed in a physician's office lab. In addition, antiviral susceptibility reagents lacked the sensitivity necessary to contemplate direct testing on a non-culture amplified specimen. Chemistry of equal or better sensitivity and directed to an independent antigen was needed, and a portable reader capable of reading multiple signal outputs, such as reflectance, fluorescence, luminescence, was missing. Accordingly, there is a need for a sensitive and rapid test for influenza drug resistance would promote a more rational use of the antiviral therapeutics.

Some embodiments provided herein include a POC test for the presence of Influenza A+B, which targets one set of influenza epitopes via immunoassay and assessing influenza drug resistance by targeting a separate influenza antigen, the neuraminidase. Combining these antigens leads to better flu detection overall, while simultaneously providing a guide for therapy.

Some embodiments provided herein include a sensitive immunoassay for nucleocapsid and a kinetic assay for measuring neuraminidase activity. In some embodiments, the kinetic assay can include a dual enzyme kinetic assay. The dual enzyme kinetic assay for neuraminidase activity with an immunoassay for nucleocapsid can include luciferase as a second enzyme and a luciferin-based conjugate as a substrate. Influenza types A and B virus possess surface glycoproteins, neuraminidases capable of hydrolyzing substrates containing alpha-ketosidically linked N-acetylneuramic acid, sometimes referred to as Neu5Ac. In some embodiments, substrates for use in a neuraminidase-based antiviral susceptibility test can be hybrid molecules (conjugates) comprised of N-acetylneuramic acid and luciferin. When luciferin is released in the presence of luciferase, light is produced in an amount directly proportional to the residual neuraminidase activity in the specimen. In some embodiments, N-acetylneuramic acid-firefly luciferin conjugates can include those used in the Cellex QFlu™ Combo kit.

Some embodiments provided herein include a reader. In some embodiments, the reader includes the reader of the Veritor™ System (Beckton Dickinson) which includes luminometry capabilities. The luminometer can be used with various test disposables including a lateral flow cartridge which is used in the Veritor™ System, and microwell strips. The additional sensitivity and disposable flexibility can be an useful option to derive a second result from the specimen currently used only to identify the presence of Influenza A or B.

Currently when influenza enters a community, a specimen is taken and a determination of influenza A or B is made by the primary care physician. The remaining specimen can be sent to a surveillance lab for drug susceptibility testing and results posted on a government website for other physicians in the community to view. While some of the methods and compositions provided herein seeks to guide the physician to the best neuraminidase inhibitor (NAI) antiviral, such embodiments can also provide an opportunity to make further improvements to basic physician office lab influenza testing in terms of sensitivity, since both neuraminidase and nucleocapsid can be measured on the same specimen. Some of the methods and compositions provided herein also provide the chance to collect more accurate antiviral resistance data for surveillance, as many leading authorities on the subject believe the true neuraminidase phenotype can change when the virus is amplified by MDCK culture, a step required by the traditional laborious $IC_{50}$ drug sensitivity assay.

Neuraminidase activity measurements with and without drug are conducted routinely in laboratories around the world as a component of influenza surveillance. While the tissue culture based neuraminidase activity assay could benefit from additional standardization, the assay is an acceptable and reliable method for determining drug resistance for a clinical specimen after sufficient quantities of virus have been generated by cell culture. Chemiluminescent substrates such as the NA-Star™ (Applied Biosystems) are routinely used to measure influenza neuraminidase activity. In contrast, some of the methods and compositions provided herein include another enzyme to the reagent cocktail, which can act on a substrate created by the neuraminidase reaction. In doing so, some of the methods and compositions provided herein amplify the signal produced by the native influenza virus enzyme. The second enzyme in turn serves to replace the culture amplification step used in the more traditional laboratory surveillance procedure. In some embodiments, an immunoassay signal from the Veritor™ System can verify sufficient viral antigen is present for the neuraminidase assay, taking the place of the laborious virus titration, a step sometimes performed when setting up $IC_{50}$ assays. When a specific signal intensity is reached in the immunoassay, the luminescent signal ratio (enzyme activity without drug:enzyme activity in the presence of drug) is valid.

Some of the methods and compositions provided herein include a platform that can be rapid, easy-to-use, and low cost. Some embodiments can target multiple testing scenarios, providing a tool for POC physician office laboratories and labs needing higher throughput. These same qualities are useful for resource-limited settings and use during pandemics.

Some of the methods and compositions provided herein include the Veritor™ System, a portable, handheld if desired, system with improved sensitivity, due in large part to a novel proprietary detector particle. See FIG. 1. The instrumented read creates the potential to be quantitative, a system attribute required for the proposed antiviral susceptibility test.

Some of the attributes of Veritor™ System that are useful for broad distribution include: 1) Ease of use by relatively unskilled caregivers and sufficient portability to push out to remote testing sites (physician offices, pharmacies, rehabilitation centers and potentially mobile use). 2) The widest possible range of patients, including a focus on the first ever Point of Care (POC) influenza antiviral susceptibility test. 3) Use in biological environments. 4) Low deployment cost. 5) Combination system used to determine Influenza A and B present in nasal swabs, nasopharyngeal wash or aspirates, having also the ability to flag drug resistant strains of influenza. As a result enhancing diagnosis, treatment and surveillance. 6) Battery powered. 7) Light weight reader with a small footprint—15 cm (W)×15 cm (H)×15 cm (D).

The lateral flow design and membranes shown in FIG. 1 are useful to integrate two or more assays involving different chemistries. Lateral flow substrates allow chemical reactions involving two distinct enzymes to be placed in proper sequence, in which buffers can be exchanged, other reagents can be prepositioned and different types of signal can be read in different regions of the lateral flow substrate.

In some embodiments, solid supports such as the nitrocellulose used in the reaction pad and the detector particle are common components in lateral flow assay devices. See e.g., U.S. Pat. Nos. 5,998,221 and 6,194,220 which each relate to quantitative lateral flow and are incorporated herein by reference in its entirety. In some embodiments, quantitative lateral flow is a useful step in verifying adequate viral antigen is available for the antiviral resistance test. In some embodiments, the lateral flow strips can use separate membranes for the specimen pad and for the conjugate pad. In some embodiment, a lateral flow strip can include a plurality of membranes. In some embodiments, a lateral flow strip can include four membranes. In some embodiments, a lateral flow strip can include four membranes in a lateral flow cassette. In other embodiments, one membrane is used for both receiving specimen and holding the dried down conjugate.

Some of the methods and compositions provided herein include a dual enzyme system. In some embodiments, components of the Cellex substrate-enzyme reagent system may be used. More details about the esterase dual enzyme chemistries can be found in the following publications: Mize et al., Dual Enzyme Cascade, Analytical Chemistry, 179, (1989) p 229-235; U.S. Pat. Nos. 4,904,583; and 4,835,099, which are each incorporated by reference in its entirety.

Figure 4:
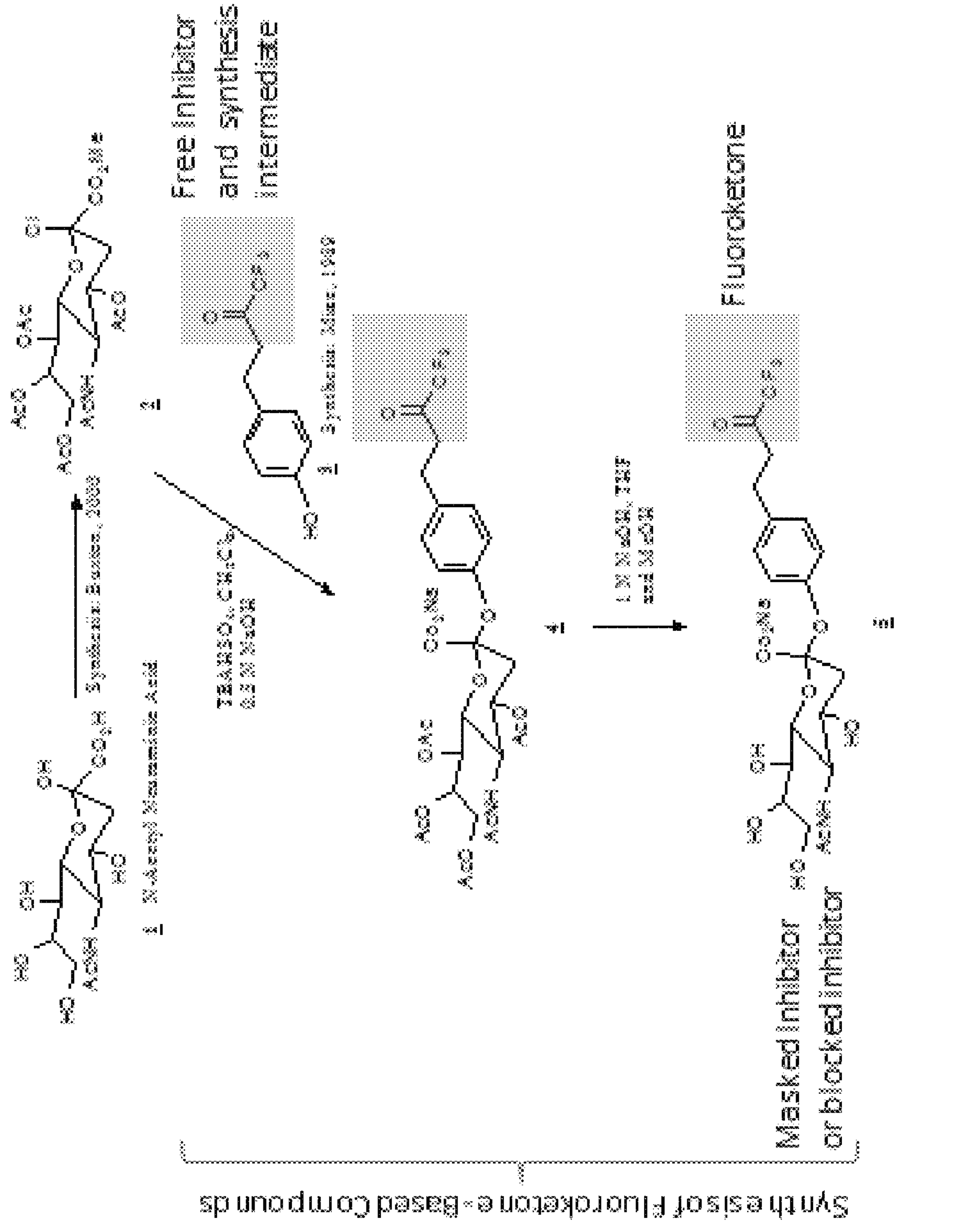
FIG. 4 depicts an embodiment of a synthesis for a masked inhibitor.

Some of the methods and compositions provided herein include modified luciferase enzymes and substrates for such enzymes including neuraminic acid-luciferin conjugates. In some embodiments, amplification can be further accomplished by introducing a different second enzyme (esterase) and a fluoroketone-based blocked (masked) inhibitor. FIG. 4 shows the synthesis for an embodiment of a masked esterase inhibitor. FIG. 4 shows an embodiment of a substrate that includes either a carbamate or carbonate linkage as the neuraminidase substrate.

Some of the methods and compositions provided herein include a range of possible format configurations. In some embodiments, complete execution of the immunoassay and dual enzyme assay can include a lateral flow format. In some such embodiments, a specimen processed by the same extraction reagent can be loaded on a lateral flow sample pad and moments later the terminal end of the lateral flow cassette can be read for the presence influenza and a recommendation for therapy can be provided as well. In some embodiments, a color change can be measured using a reflectance reader. In some embodiments, a measurement, such as a reflectance measurement, can be taken direct from the lateral flow membrane for influenza detection, and another type of measurement, such as a chemiluminescence, fluorescence, or chromophore measurement, can be taken for drug susceptibility. In some embodiments, a measurement can be taken using a reader refers to an instrument for detecting and/or quantitating data, such as on test strips. Such readers are disclosed and described in U.S. Pat. Nos. 6,267,722, 6,394,952 and 6,867,051, which are incorporated by reference in their entireties. In some embodiments, a reflectance reader refers to an instrument adapted to read a test strip using reflected light, including fluorescence, or electromagnetic radiation of any wavelength. Reflectance can be detected using a photodetector or other detector, such as charge coupled diodes (CCD).

Both immunoassay and susceptibility signal may be observed using a common detector, such as a CCD camera. In some embodiments, the immunoassay and susceptibility assays could be read using different detectors, such as a CCD and photomultiplier tube. In some embodiments, portable cooled CCD cameras for quantitative "on field" chemiluminescent measurements can be used. In some embodiments, a chemiluminescent antiviral susceptibility assay can also be read by a PIN diode with a low-noise amplifier In some embodiments, where a first enzyme reaction in the dual enzyme assay is not compatible with the immunoassay reagents, the front end of the dual enzyme assay is performed offline and a partially processed specimen with cleaved substrate is loaded on to the lateral flow sample pad, which can travel down the lateral flow strip by capillary action to a solid support containing luciferase and the other reagents necessary to generate a luminescent signal. In this configuration, the immunoassay and susceptibility signal may be read using a common detector, such as a CCD camera. In some embodiments, the immunoassay and susceptibility assays could be read using different detectors, such as a CCD and photomultiplier tube.

In some embodiments, dual enzyme assays on lateral flow may be achieved by submerging the section of the processed lateral flow cassette containing cleaved luciferin into a well with luciferase and other reagents needed to produce a luminescent signal. Light produced from the dual enzyme assay is then measured by a Luminoskan TL Pus or equivalent tube luminometer.

In some embodiments, the immunoassay is conducted and read on a lateral flow cassette and a dual enzyme assay is conducted and read on a well strip. The two assays may share a common extracted specimen, but are executed on different formats, then read on a common instrument that can accommodate lateral flow reflectance and well strip chemiluminescence (or fluorescence or other optical signal). Both immunoassay and susceptibility signal may be observed using a common detector, such as a CCD camera, or the immunoassay and dual enzyme assays could be read using different detectors, such as a CCD and photomultiplier tube.

Figure 2:
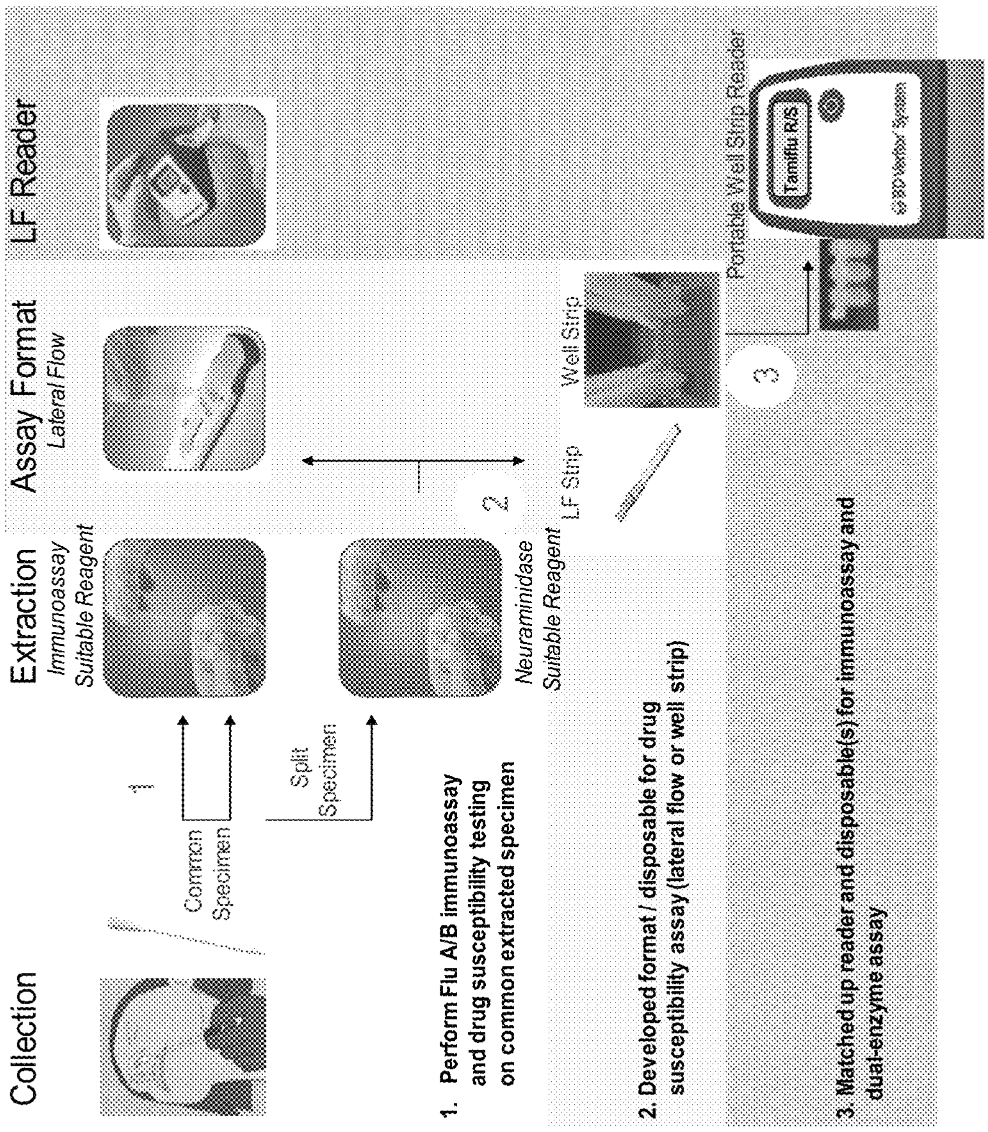
FIG. 2 depicts an embodiment of a workflow for combining a lateral flow immunoassay and a drug susceptibility assay.

General Approach to Determine an Embodiment:

As shown in FIG. 2, applicants explored several options for running the flu-typing and antiviral sensitivity test on a single sample. In one embodiment, the specimen was split and treated with two different extraction buffers, with each portion of the specimen being used in only one assay. A limitation of this approach is that in some situations not enough specimen was available to run both the Flu ID and the AST assays. In one embodiment, a common extraction reagent and buffer which could be used in both assays was tested. A limitation of this approach is that conditions for the immunoassay and the kinetic assay are different, making use of a common buffer less than optimal. In another embodiment, a single extraction buffer appropriate for either the Flu ID or the AST assay was used, with conversion of the buffer to the opposing assay in real-time. This embodiment provided sufficient sample volume and sensitivity for both assays. FIG. 2, also shows multiple embodiments of assay formats for both flu ID and susceptibility testing that were developed. Appropriate readers and disposable(s) for the combined lateral flow immunoassays and dual-enzyme assays are used (e.g. if a well strip is used for the AST, a separate well strip reader may be used, whereas if a lateral flow strip is used, a single lateral flow reader may be used for both tests).

In some embodiments, a common extraction reagent for both immunoassay and antiviral resistance measurements is used.

In some embodiments, a lateral flow format is used for both immunoassay and dual enzyme assay in which the antiviral resistance measurement on the neuraminidase that passes through the nitrocellulose pad. In some embodiments, the assay may be performed on the ~150 μl specimen which often remains after the immunoassay lateral flow cartridge has been loaded. In some embodiments, one or both volumes may be measured in a well strip as a homogenous assay.

In some embodiments, a system includes a luminometer, such as the Tropix or Bethold, a portable luminometer such as the HG-2 from the Shanghi Huguo Science Instrument Company.

In some embodiments, sources of virus can include frozen, known flu positive, clinical specimens to verify a functional kinetic and immunoassay in the presence of human nasal secretions.

Dual Enzyme Antiviral Susceptibility Assay

Figure 3:
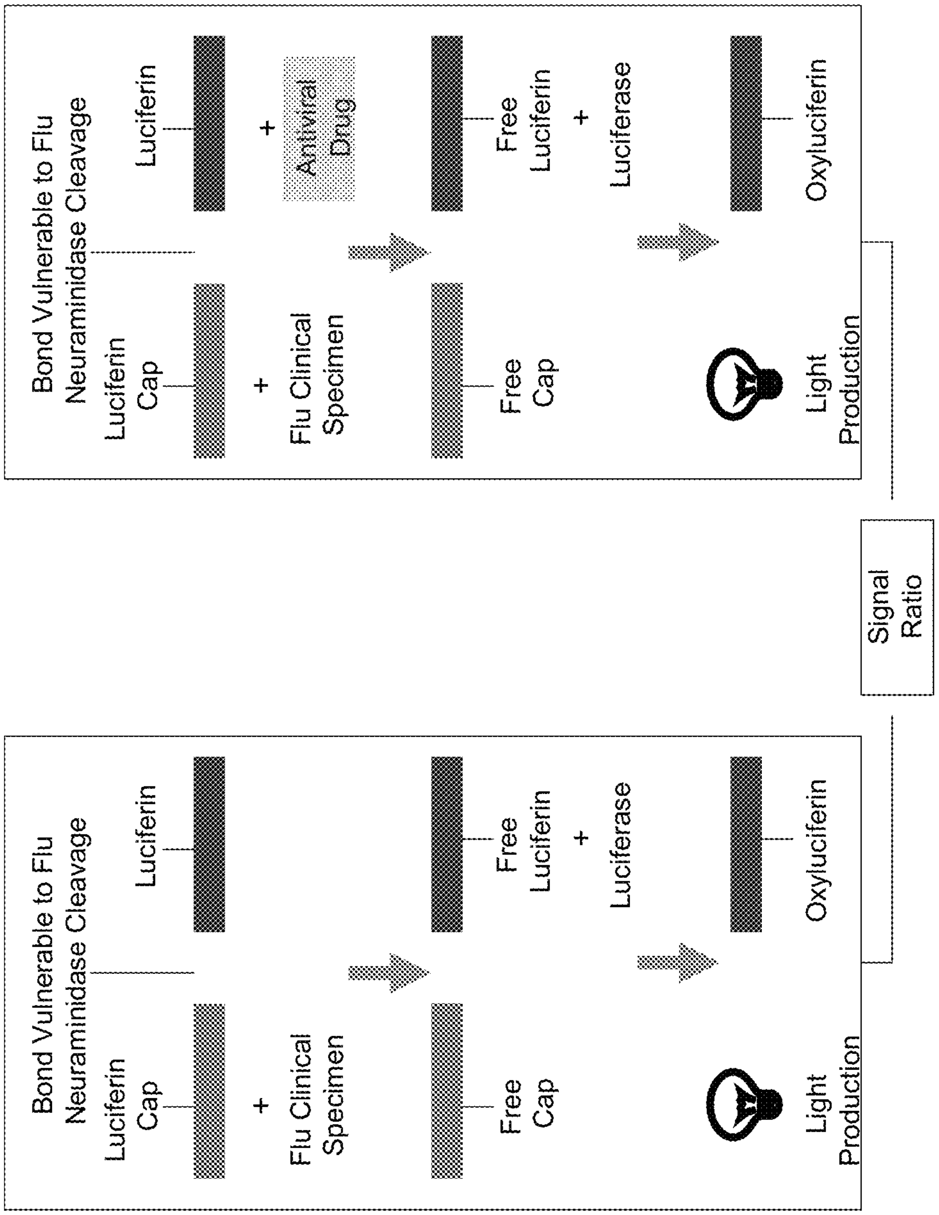
FIG. 3 depicts an embodiment for determining signal ratio in a drug susceptibility assay

As shown in FIG. 3, some embodiments of a dual enzyme kinetic assay for neuraminidase activity can include luciferase as the second enzyme and a luciferin-based conjugate as substrate. Yolken reported on fluorescent substrates for neuraminidase in 1980. Buxton reported on chemiluminescent substrates for neuraminidase in 2000 and Hamilton performed a side by side comparison of the FDA Approved ZestatFlu-II Test in 2004, which uses a chemiluminescent neuraminidase substrate for influenza identification. No single enzyme-single substrate system has evolved into a robust drug susceptibility test suitable for performance in a physician's office laboratory. This may be a matter of sensitivity, addressable by a better signal amplification system. Some embodiments provided herein include a dual-enzyme system, which involves a luciferin conjugate. Once acted upon by the influenza neuraminidase the conjugate releases free luciferin, which in turn is acted upon by luciferase. In the embodiments disclosed herein, such dual enzyme chemiluminescent systems can provide sufficient amplification for a POC antiviral susceptibility diagnostic. An example of reagents useful with the methods and compositions provided herein include reagents used in the QFlu™ Combo Test by Cellex.

Demonstrating Ability to Perform Flu A/B Immunoassay and Drug Susceptibility Testing on a Common Extracted Specimen Some embodiments provided herein include demonstrating which assay reaction steps/reagents are compatible when performed over same time frame and in close proximity, if not in the same space. In some embodiments, the immunoassay for nucleocapsid and dual-enzyme assay for neuraminidase activity can be monitored closely for any loss in sensitivity, specificity, assay range, resolution and time-to-result. Not all steps from the two assays need to be compatible to be successful. In some embodiments, the Veritor™ immunoassay reagents and the current Dual-Enzyme reagents used in the Cellex QFlu™ assay (currently deployed for surveillance purposes) are utilized in the disclosed methods, compositions, kits, devices and systems. One reagent evaluated was the lysis reagent used for both assays. In some embodiments, the lysis reagent from the Veritor™ immunoassay is used for preparation of a sample used in both the Flu A/B and drug sensitivity test. In another embodiment the lysis reagent from the Cellex QFlu™ assay is used is used for preparation of a sample used in both the Flu A/B and drug sensitivity test.

Interference Screening for the Antiviral Susceptibility/Resistance Assay

Influenza types A and B virus possess surface glycoproteins, neuraminidases capable of hydrolyzing substrates containing alpha-ketosidically linked N-acetylneuramic acid, sometimes referred to as Neu5Ac. Substrates evaluated for use in the neuraminidase-based antiviral susceptibility test included hybrid molecules (conjugates) comprised of N-acetylneuramic acid and luciferin. When luciferin is released in the presence of luciferase, light is produced in an amount directly proportional to the residual neuraminidase activity in the specimen. In one embodiment, the N-acetylneuramic acid-firefly luciferin conjugates used in the Cellex QFlu™ Combo kit, which is currently distributed for surveillance applications, was evaluated. In some embodiments, benchmarking experiments are performed with a cultured viral stock, whereby two separate reactions are conducted for each test condition, one reaction for example containing the antiviral (Ex: Oseltamivir) and the other neuraminidase activity measurement performed without antiviral inhibitor. Control specimens can be assayed by the rapid method under development and by one of the recommended WHO IC50 methods. In some embodiments, screening of antiviral susceptibility reagents may be conducted in a microwell, tube or cuvette or plate and read for chemiluminescence or fluorescence. Screening can be conducted with antiviral resistant and sensitive strains of influenza. When expeditious, pure neuraminidase may be spiked into specimen and used in interference screening. Frozen known positive clinical specimens can also be tested on a regular basis primarily to make sure other components of the nasal secretion are not interfering with the dual-enzyme assay.

Interference Screening for the Immunoassay

In some embodiments, screening for influenza detection (immunoassay) reagents can be performed in the lateral flow format and read for reflectance, as currently performed in the FDA approved CLIA Waived Veritor™ Product. The BD Veritor™ immunoassay uses two monoclonal antibodies directed at the influenza nucleocapsid. One antibody is immobilized to the surface of a proprietary gold particle and the other is immobilized to nitrocellulose in the lateral flow cassette. The amount of signal detected on the nitrocellulose reaction strip is proportional to the amount of influenza virus in the specimen. Testing Dual-Enzyme reagents for potential interference to the Veritor™ immunoassay, can be performed in the presence of Influenza A (flu A/PR/8/34) and Influenza B (flu B/Lee/40) positive samples prepared to yield a final concentration corresponding to a moderate positive (~5 times level of detection). Test interference may be seen in the form of a false positive result with Influenza A or Influenza B negative samples or a false negative result with an Influenza A or Influenza B positive sample. Only those dual enzyme reagents which do not exhibit interference can be advanced. When expeditious, pure nucleocapsid can be spiked into specimen and used to screen for performance.

Other Dual Enzyme Chemistry

Other dual enzyme reagent systems include substrates similar to the Cellex system that includes a N-acetylneuramic acid and luciferin conjugate components but utilize a different linker. In some embodiments, a different luciferase enzyme may be used.

Determining Format/Disposable for Drug Susceptibility Assay

Some embodiments of the methods and compositions provided herein include selecting appropriate format for combined assays. In some embodiments, where the chemistry is found to be compatible, then complete execution of the immunoassay and dual enzyme assay may be best handled on the lateral flow format. When lateral flow format is used for both assays, a specimen processed by the same extraction reagent can be loaded on a lateral flow sample pad and moments later the terminal end of the lateral flow cassette can be read for the presence of influenza, including A/B type, and a recommendation for therapy based on drug susceptibility can be provided as well. A reflectance measurement can be taken direct from the lateral flow membrane for influenza detection and a chemiluminescent measurement taken for drug susceptibility. In some embodiments, a portable cooled CCD cameras for quantitative "on field" chemiluminescent measurements can be used.

In some embodiments, wherein a first enzyme reaction in a dual enzyme assay is not compatible with other immunoassay reagents, the front end of the dual enzyme assay is performed offline and a partially processed specimen with cleaved substrate is loaded on to the lateral flow sample pad, which can travel down the lateral flow strip by capillary action to a solid support containing luciferase and the other reagents necessary to generate a luminescent signal.

In some embodiments, dual enzyme assays on lateral flow may be achieved by submerging the section of the processed lateral flow cassette containing cleaved luciferin into a well with luciferase and other reagents needed to produce a luminescent signal. Light produced from the dual enzyme assay is then measured by a Luminoskan TL Pus or equivalent luminometer.

In some embodiments, the immunoassay is conducted and read on a lateral flow cassette and a streamlined Cellex Qflu™ Combo assay is conducted and read on a well strip. The two assays may share a common extracted specimen, but are executed on different formats, then read on a common instrument that can accommodate lateral flow reflectance and well strip chemiluminescence. In some embodiments, two separate instruments are used. In some embodiments, the single or multiple devices are portable, battery powered devices with a small footprint, suitable for a placement in a doctor's office, for example sized to fit on a counter top or a portable medical stand.

System Validation

A test set of 20 influenza strains can be cultured and enumerated, allowing the final combination platform (integrated disposable, reader and reagents) to be assayed for sensitivity down to concentrations of 10E3 viral particles (defined in $TCID_{50}$/ml or $CEID_{50}$/ml units). The test set of 20 strains can contain a balance of influenza A and B strains. Influenza A strains can be a mix of Influenza H1N1 and H3N2. The test set can contain TamiFlu™ resistant and susceptible strains. The test set can also include strains resistant and susceptible to a second NAI drug. To benchmark progress and the final integrated system, nearly 100 frozen known positive clinical isolates can be used.

Antivirals for Development and Validation

TABLE 1 provides example NAI (neuraminidase inhibitor) antivirals useful with the methods and compositions provided herein. Since a population cannot rely on newly circulating strains of influenza to always be sensitive to Oseltamivir and Zanamivir, generating data in the POC antiviral susceptibility diagnostic with the Biota drug is desirable.

TABLE 1

| NAI Antiviral and Manufacturer |
|---|
| Tamiflu ™ |
| Oseltamivir Carboxylate (active)/Oseltamivir phosphate (prodrug), oral delivery, based on DANA w\ knowledge of Zanamivir |
| Roche, USP, Sequoia Res Labs |
| Relenza ™ |
| Zanamivir, inhaled, based on DANA -Higher affinity than DANA |
| GSK |
| Inavir ™ |
| Laninamivir octonoate, inhaled, $2^{nd}$ generation = long acting NAI, based on Zanamivir |
| Biota Pharmaceuticals, recent Biota and NABI Merger/Daiichi Sankyo Co, Limited |
| Rapiacta ™/Peramiflu ™ |
| Peramivir, parenteral, based on DANA, has features of Zanamivir and Oseltamivir |

DANA = 2,3,-dehydro-2-deoxy-N-acetylneuraminic acid

McKimm-Breschkin (2012) Influenza neuraminidase inhibitors: Antiviral action and mechanisms of resistance. Influenza and other Respiratory Viruses 7 (Suppl. 1), 25-36.

Wathen M, Barro M, Bright R, (2012) Antivirals in seasonal and pandemic influenza - future perspectives. Influenza and Other Respiratory Viruses 7 (Suppl), 76-80.

Influenza Strains, Isolates and Control Collections

TABLE 2 contains example specific phenotypes and genotypes for use with some embodiments of the methods and compositions provided herein. Influenza A and Influenza B Strains (BSL-2), both resistant and susceptible to neuraminidase drugs can be obtained for development. In some embodiments, methods and compositions provided herein include major Flu A subtype neuraminidases, as well as Flu B neuraminidases.

TABLE 2

| | |
|---|---|
| Extensively Characterized Drug Resistant Strains ~20 isolates | ISIRV 8-Member Panel<br>Mix of resistant Flu B WT + Genotype D1973, Flu A (H3N2) WT + Genotype E119V, Flu A (H1N1) WT + Genotype H275Y, Flu A (H1N1 pdm09) WT + Genotype H275Y<br>Oselt Resistance<br>A/Washington/29/2009(H1N1pdm) H275Y Oselt (IC50 = 1462)<br>A/Georgia/20/2006 (H1N1) H274Y Oselt (IC50 = 383)<br>A/Massachusetts/5/2007 (H1N1) H274YOselt (IC50 = 258)<br>A/Texas/12/2007 (H3N2) E119VOselt (IC50 = 9.18)<br>Zana Resistance<br>A/Montana/8/2007 (H3N2) D151V/D Zana (IC50 = 191.9)<br>Oselt+ Zana Resistance<br>B/Hong Kong/36/2005 B) R371K Oselt (IC50 = 1778) Zana (IC50 = 154)<br>Oselt resistant (recovered from pts with no prior history of oselt therapy |
| Known Flu Positives Up to 100 isolates | An assortment of known flu positive cultures which may have been recovered from aspirates, nasal pharyngeal wash, swabs, etc. In many cases BD can only know as Flu A/B. In some cases the neuraminidase and hemaglutinin designation may be known. |
| Flu Negative NPW Up to 10 collections | Nasal pharyngeal wash collected for negative control purposes and diluent for spiked flu antigen |

Benchmark Testing

Some embodiments provided herein include the performance of the $IC_{50}$ for the single point QFlu™ Combo and Immunoassays. The Veritor™ and QFlu™ systems can be used according to package inserts. There are many options for $IC_{50}$ prepared kits, such as the NA-Star™ Kit from Applied Biosystems/Life Technologies. TABLE 3 provides examples of sources and part numbers for the supplies that can be used in the antiviral testing.

TABLE 3

| Description | Vendor | Cat. # |
|---|---|---|
| NA-Star ™ Influenza NAI Resistance Detection Kit (Primary) | Applied Biosystems | 4374348 |
| NA-XTD ™ Influenza NAI Resistance Detection Kit (Alternate) | | 4457534 |
| NA-Fluor ™ Influenza NAI Resistance Detection Kit (Alternate) | | 4457091 |
| NA-Star ™ + NA-XTD ™ Detection Microplates | Applied Biosystems | 4374349 |
| Intact Cellex QFlu ™ Combo Kits used per package insert in benchmarking | Cellex | |
| Intact BD Veritor ™ Kits used per package insert in benchmarking | Becton Dickinson | |

$IC_{50}$ Methods

Some embodiments of the methods and compositions provided herein can be compared with a chemiluminescent NAI assay conducted with the commercially available NA-Star® Kit (Applied Biosystems, Foster City, Calif.) which includes NA-Star® buffer (26 mM MES, 4 mM CaCl2, pH 6.0), NA-Star® substrate, NA-Star® accelerator, and 96-well solid white plates. Catalogue 4374348 and 4374349. Further details of $IC_{50}$ method, preparation and analysis can be found in ANTIMICROBIAL AGENTS AND CHEMOTHERAPY, September 2008, p. 3284-3292 Vol. 52, No. 9, which is incorporated herein by reference in its entirety.

Specimen Selection (Swab Vs. Wash Vs. Aspirate) and Impact on Assay Sensitivity

Some embodiments include three specimen options (direct testing from swabs vs. testing from nasopharyngeal wash or aspirates). Some embodiments include testing from frozen specimens and culture, and the ability to perform the nucleocapsid immunoassay and neuraminidase activity assay from a single collection.

Testing Direct from Swabs

Some embodiments of the methods and compositions provided herein include the use of swabs to collect specimens. The first Veritor™ immunoassay is based on a dry swab collection whereby the entire specimen is intentionally committed to a "Processing Reagent" (400 μl volume) and the package insert calls for the specimen to be applied to the lateral flow strip within an hour. Typically several hundred microliters remains after an ~80 μl volume is loaded on to an lateral flow cassette, leaving a large amount of unused processed antigen which can be directed to the antiviral susceptibility test. While this specimen processing path does not portion out a sample for viral culture, in some embodiments, both immuno and kinetic assays can perform at or near their peak level of detection with some specimen remaining which can be supplemented with nucleic acid stabilizer for later PCR detection.

Testing Nasopharyngeal Wash/Aspirates

The Veritor™ platform includes a method in which a concentrated mucolytic reagent is added to the collected specimen at 3 parts to 1 part prior to loading on a lateral flow cassette. Three hundred \ microliters of each organism suspension is added to the unitized tube containing RV Reagent C or RV Reagent D as sold by BD (for example in the kit for the Veritor™ System for Rapid Diagnostics of Flu A&B (Product No. 256045). More than 10 preservation-transport media have been tested with these wash/aspirate specimens successfully. Examples of preservation-transport media include: M4RT, M4, M5, UTM, Ames Medium (liquid), Bartel Vira Trans™ Medium, Hanks Balanced Salt Solution, Normal Saline, Phosphate Buffered Saline. M4RT media is pH 7.3 at 25° C. and contains Hank's balanced salts: $CaCl_2$, $MgCl_2$-$6H_2O$, $MgSO_4$-$7H_2O$, KCl, $KH_2PO_4$, NaCl, $Na_2HPO_4$-$7H_2O$, glucose. Therefore, in some embodiments, a sample for virus propagation can be collected with a nasopharyngeal wash/aspirate before mucolytic agent is added. A possible antigen dilution affect can be taken into consideration when using nasopharyngeal wash/aspirate specimens. The Veritor™ assay has greater sensitivity than any other rapid assay on the market.

Chemiluminescence Methods and Metrics to Access Sensitivity

Chemiluminescence methods useful with the methods and compositions provided herein include those disclosed in U.S. Pat. Nos. 8,221,976; 8,163,237; 7,947,820; 7,642,060; 7,291,488; 5,736,365; 5,639,428; 5,561,044; 5,518,884; 5,470,723; 5,457,027; 5,314,801; 5,017,473; and 4,810,631, each of which is incorporated by reference in its entirety. In some embodiments, the metrics of a dual enzyme test is substantially similar to the metrics, such as level of detection for flu virion, obtained using the Veritor™ immunoassay. In some embodiments, the chemistry for detecting the presence of neuraminidase can produce sufficient signal at a $10^3$ $TCID_{50}$ to also allow for a robust 5:1 ratio to be observed between reactions performed with drug and w\o drug. In some embodiments, both sensitivity and long linear range can be assessed. In some embodiments, the Cellex may be used.

Certain Chemistries

Figure 12:
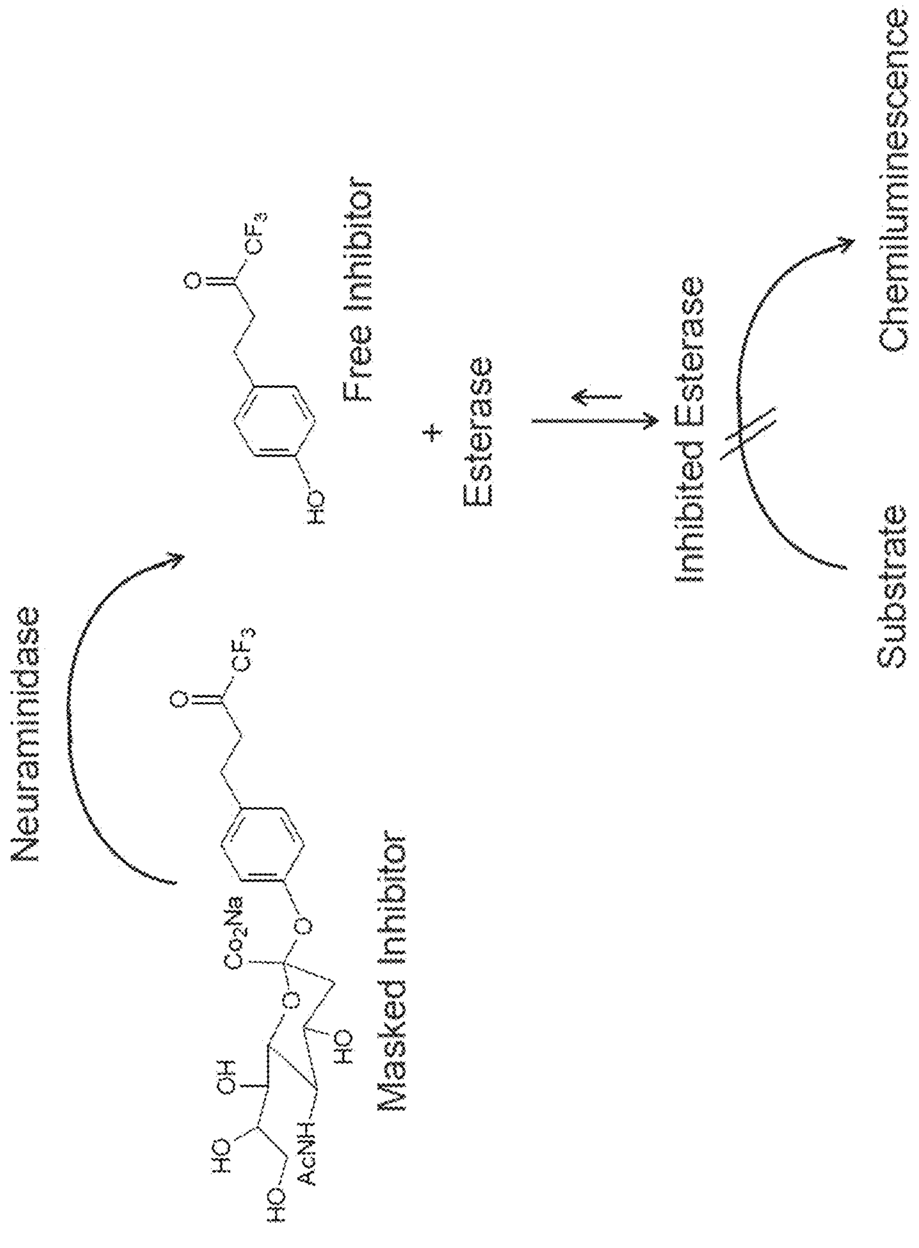
FIG. 12 depicts an embodiment of a complete Dual Enzyme Cascade involving masked and free inhibitor.

FIG. 12 shows an esterase-based chemistry that can be used with the compositions and methods provided herein to assay neuraminidase activity. Methods useful with embodiments of the methods and compositions provided herein include those disclosed in the following: Mize et al., Dual Enzyme Cascade, Analytical Chemistry, 179, (1989) p 229-235; U.S. Pat. Nos. 4,904,583; 4,835,099, which are each incorporated herein by reference in its entirety. Some embodiments include modified luciferase enzymes and substrates thereof, such as modified neuraminic acid-luciferin conjugates. Other inhibitors which can be used include the following:

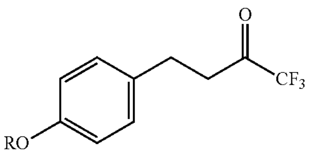

R = H Esterase Inhibitor
R = NANA Masked Esterase Inhibitor

Some Possible Beta-Thio Variants Inhibitor/Masked Inhibitor

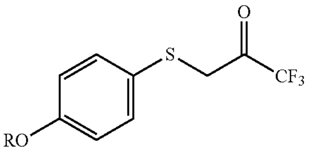

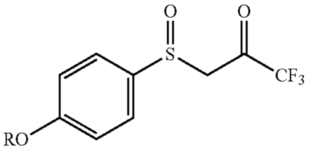

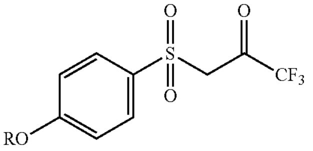

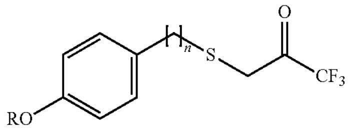

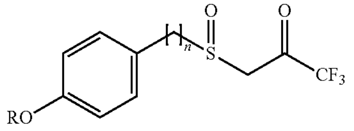

n = 1-3

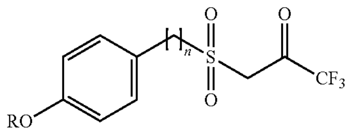

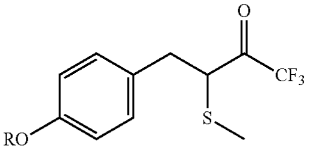

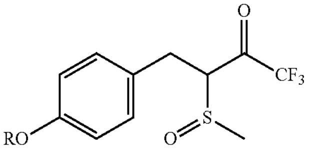

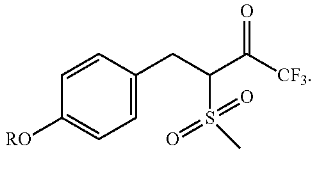

The compound in FIG. 12 has the trifluoroketone in the para position. More esterase inhibitors include 1,1,1-Trifluro-4-(4-hydroxyphenyl)butan-2-one (para); 1,1,1-Trifluro-4-(3-hydroxyphenyl)butan-2-one (meta); and 1,1,1-Trifluro-4-(2-hydroxyphenyl)butan-2-one (otho).

Alternative masked inhibitor substrates for use in the embodiments disclosed herein include those having the trifluoroketone in the -meta and -ortho positions as provided below:

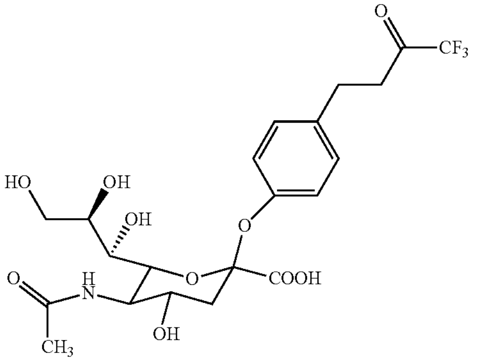

para-substituted

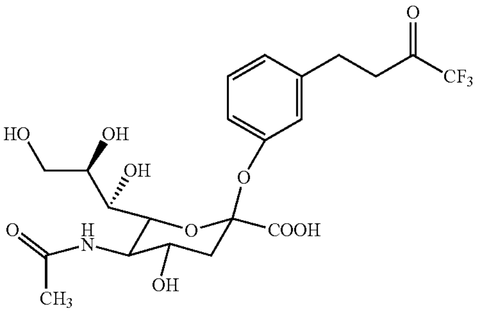

meta-substituted

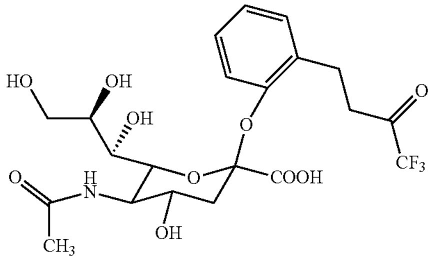

ortho-substituted

In another embodiment, a 4,7 methylated N-acetyl-neuraminic acid (NANA)-trifluoroketone could be used in the DE masked inhibitor assay, with more specificity to the influenza neuraminidase.

Some embodiments include a masked inhibitor compound for use in a dual enzyme influenza neuraminidase sensitivity assay having the structure of Formula (I):

(I)

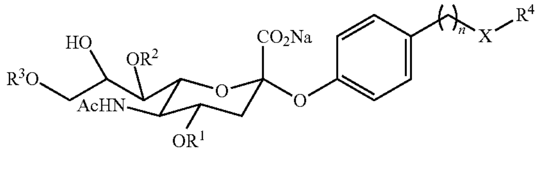

wherein: $R^1$, $R^2$ and $R^3$ are each independently hydrogen or $C_{1-5}$ alkyl; n is 0, 1, 2 or 3; $R^4$ is $—(CH_2)_mC(=O)CF_3$; m is 0 or 1; X is $—S(O)_z—$ or $—CH(R^5)—$; $R^5$ is $—S(O)_zCH_3$; and z is 0, 1 or 2.

In some embodiments, a compound of Formula (I) is selected from the group consisting of:

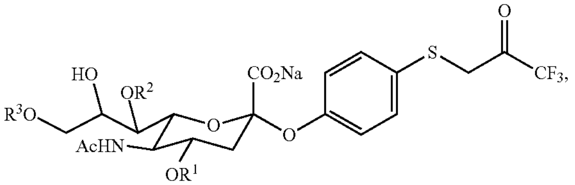

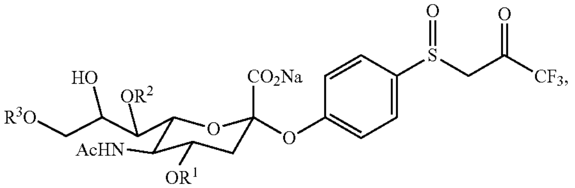

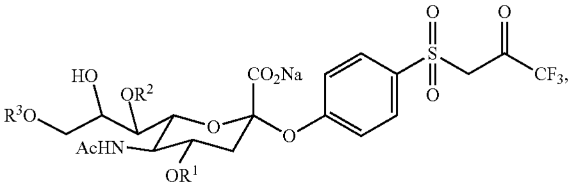

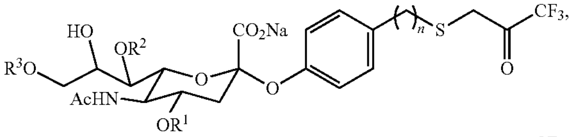

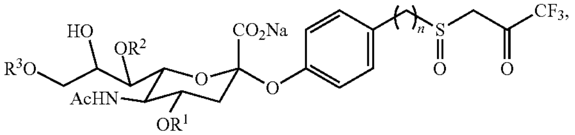

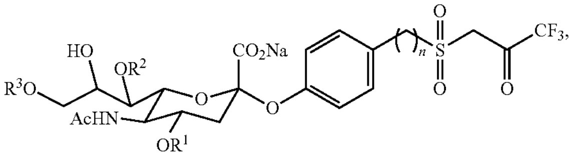

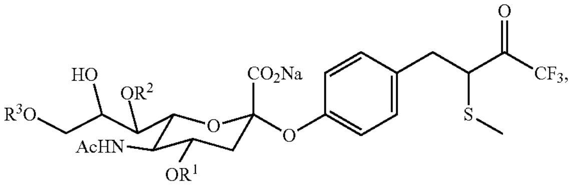

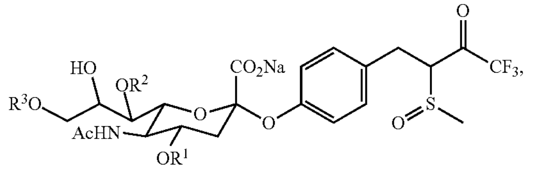

and

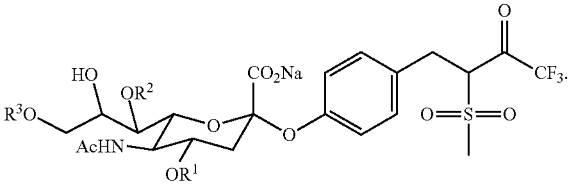

DNA Sequencing

In some embodiments, genotype data is obtained from a flu virion of a specimen. In some embodiments, a particular virus isolate may produce a drug sensitivity profile with the benchmark tissue culture $IC_{50}$ method different from a profile from the rapid POC test. The different profiles may be due to a mutation at residues within the neurimidase active site and known to confer resistance in specific influenza subtypes or framework substitutions elsewhere in the NA. Methods to sequence nucleic acids from specimens are well known in the art.

Interference from Other Pathogens

In some embodiments, it is envisaged that some specimens from patients suspected of a having flu infection may contain other pathogens that produce a neuraminidase. TABLE 4 provides examples of pathogens most commonly found in flu positive clinical specimens.

TABLE 4

| Reference | Frequent Coinfections |
|---|---|
| Peci et al., Community-acquired respiratory viruses and co-infection among patients of Ontario sentinel practices (2012) 1750-2659 | Influenza with RSV<br>Influenza with enterovirus<br>Influenza with rhinovirus<br>Influenza with para influenza 1, II and III<br>Influenza with coronavirus<br>Influenza with adenovirus |
| Wang et al., Influenza and Bacterial Pathogen Coinfections in the 20$^{th}$ Century, Interdisciplinary Perspectives on Infectious Diseases, Volume 2011 (2011) Article ID 146376 | Influenza with *S. pneumonia* |
| Shimasaki et al., Rapid Diagnostics: the detection of neuraminidase activity as a technology for high-specificity targets, The Royal Society, (2001) 356, 1925-1931<br>By ZymeTx Inc, makers of the ZstatFlu Dx. | Para influenza Type 1<br>Para influenza Type 2<br>Para influenza Type 3<br>Mumps Virus<br>Respiratory Virus<br>Adenovirus |

TABLE 5 provides examples of pathogens that can be tested in specimen interference testing. Such pathogens can be tested for any effect on the methods and compositions provided herein. Interference tests with whole virus or purified neuraminidase. These pathogens can be assayed at concentrations expected to be present in clinical collections.

TABLE 5

| | |
|---|---|
| Virus | Human Respiratory Syncitial Virus , Strain 9320 (ATCC- VR-955) |
| | Human Para influenza Virus 1, Strain C35 (ATCC VR-94) |
| | Human Para influenza Virus 2, Strain Greer (ATCC VR-92) |
| | Human Para influenza Virus 3, Strain C243 (ATCC VR-93) |
| | Human Coronovirus, Strain OC43 (ATCC 1558) |
| | Human Rhinovirus 17, Strain 33342 (ATCC VR-1633) |
| | Human Enterovirus 71, Strain H (ATCC 1432) |
| | Human Adenovirus 1, Strain Adenoid 71 (ATCC VR-1) |
| Bacteria | *Streptococcus pneumonia* (ATCC-6301) |

In some embodiments, samples can include nasopharyngeal washes, aspirates and swabs.

Detecting Influenza Type A or Influenza Type B

Some of the embodiments provided herein include detecting the presence of an influenza type A virus or an influenza type B virus in a specimen. Some embodiments include the use of an immunoassay to identify viral antigens that can distinguish between flu types, such as A/B. In some embodiments, the antigen is a nucleocapsid. In some embodiments, the immunoassay comprises a sandwich assay. In some such embodiments, a first antibody specifically binds to a target antigen, and the bound antigen and first antibody then specifically bind to a second antibody which produces a signal. In some embodiments, the signal is colorimetric, fluorescent, chemiluminescent, and radioactive. In some embodiments, an immunoassay can include lateral flow system. In some embodiments, a test strip comprises the immunoassay. Systems and compositions useful with the methods and compositions provided herein include the Veritor™ System for rapid detection of Flu A+B (Becton Dickinson). In some instances the output from the test strip will be reflectance. In some embodiments, the output from the test strip with be a color change that can be measured using a reflectance reader. In addition to lateral flow immunoassay formats, embodiments for determining type-A or type-B influenza viruses may comprise molecular and immuno detection in solution phase, on substrates such as membranes, surfaces, and particles. In some embodiments, microwell ELISAs, nanotag-magnetic separation assays, and particle agglutinations. An example of a molecular detection assay includes Xpert® Flu System (Cephied, Sunnyvale, Calif.). Embodiments that include nanotags, include surface-enhanced Raman spectroscopy (SERS) nanotags. See e.g., ACS Nano, 2009, 3 (10), pp 2859-2869, which is incorporated herein by reference in its entirety. Embodiments that include particle agglutination are well known and include contacting an antigen in a fluid with antigen-binding elements, such as antibodies which are coated on particles. See e.g. U.S. Pat. No. 4,590,169 which is incorporated herein by reference in its entirety.

Some of the embodiments provided herein include detecting the presence of an influenza type A virus or an influenza type B virus in a specimen include non-immunoassay methods. In some embodiments, the presence of an influenza type A virus or an influenza type B can be detected using nucleic acid-based methods, such as PCR, nucleic acid hybridization, and nucleic acid sequencing.

Measuring Neuraminidase Activity

Some embodiments provided herein include detecting and/or measuring neuraminidase activity in a sample. In some embodiments, the neuraminidase is a viral neuraminidase, such as an influenza type A or type B neuraminidase. In some embodiments, the enzyme being detected is a sialidase. In some embodiments, neuraminidase activity can be measured using a dual enzyme assay. Reagents useful with some embodiments of the methods and compositions provided herein include those of the QFlu™ NI Assay (Cellex, Inc., Maryland) and the QFlu™ Combo Assay.

In some embodiments, a substrate for neuraminidase is converted to a substrate for a second enzyme, such as an esterase, such as luciferase. In some embodiments, a substrate for neuraminidase includes conjugates of derivatives of N-acetylneuraminic acid (sialic acid) and derivatives of luciferin. In some embodiments, conjugates between N-acetylneuraminic acid or its derivatives and luciferin, are linked together through a glycoside bond via an —OH group on the sugar ring of the N-acetylneuraminic acid. In some embodiments, the position on the sugar ring is the 2' position since this is the glycoside bond favored by influenza neuraminidase. Examples of sialic acid derivatives include 4-alkyl or 7-alkyl or 4,7 alkyl N-acetylneuraminic acids (e.g. those described in U.S. Pat. Nos. 6,303,764 and 6,420,552, 6,680,054 which are incorporated herein by reference in their entireties). One example is 4,7 methylated N-acetylneuraminic acids-firefly luciferin conjugate. Embodiments of such conjugates are provided in U.S. Pat. No. 7,893,272 which is incorporated by reference herein in its entirety. In some embodiments, conjugates used as neuraminidase substrate can be represented by the following formula shown for the Na salt:

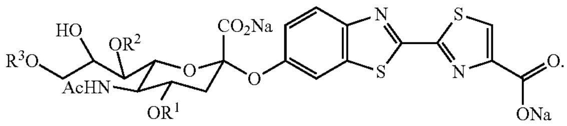

In some embodiments, R1, R2, R3 are each, independently of one another, hydrogen or alkyl having 1-5 carbon atoms.

In some embodiments, a substrate for neuraminidase is converted to an inhibitor for a second enzyme, such as an esterase, such as luciferase. In some embodiments, a substrate for neuraminidase includes conjugates of derivatives of N-acetylneuraminic acid (sialic acid) and derivatives of a trifluoromethylketone (CF3). Derivatives of N-acetylneuraminic acid are described above. In some embodiments, a substrate for neuraminidase is:

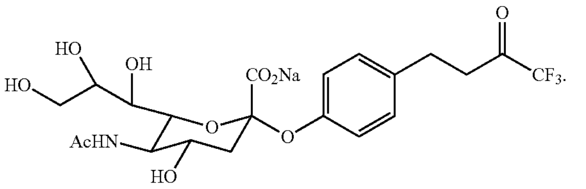

In some embodiments, the trifluoromethylketone inhibitor includes:

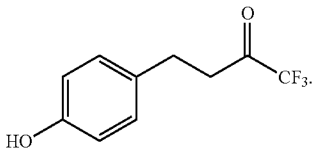 [SMILES: O=C(CCc1ccc(O)cc1)C(F)(F)F]

In some embodiments, in which a substrate for neuraminidase is converted to an inhibitor for a second enzyme, such as an esterase, the substrate is also known as a masked inhibitor. Examples of masked inhibitors useful with some of methods provided herein are disclosed herein.

An example synthesis is shown in FIG. 4. In some embodiments, a sample can contain a neuraminidase from a source other than an influenza virus. In some embodiments, an undesired neuraminidase is inhibited using specific antibodies and inhibitors. The undesired neuraminidase activity is inhibited using specific polyclonal or monoclonal antibodies. For example, for detection of influenza viral neuraminidase, the non-specific neuraminidase activity from likely contaminating organisms in the sample such as bacterial species *Streptococcus pneumoniae* and *Actinomyces viscosus* are inhibited using antibodies specific for the neuraminidases from these sources. This approach is possible because neuraminidases from different organisms have distinct amino acid sequences, which permits the generation of species-specific, or sub-species-specific, neuraminidase antibodies. For example, specific antibodies are commonly used to differentiate neuraminidase subtypes of influenza virus in neuraminidase neutralization assays.

Combination Assays

Some embodiments provided herein include combination assays in which a sample is assayed for (1) identification of type A or type B influenza virus in the sample; and (2) sensitivity of the influenza virus neuraminidase to certain antiviral drugs. In some embodiments, the immunoassay for identification of type A or type B influenza virus in the sample is performed in a buffer that is different from the assay to measure sensitivity of the influenza virus neuraminidase to certain antiviral drugs.

In some embodiments, a specimen is obtained. In some embodiments, specimens can include nasopharyngeal washes, aspirates and swabs. In some embodiments, there may be insufficient quantities of a specimen to prepare a several initial samples in different buffers. In some embodiments, a specimen is placed in a first buffer to obtain a first test sample for a first assay. In some embodiments, the first test sample comprises a buffer that is incompatible with a second assay. For example, the first buffer may inhibit a second assay. In some such embodiments, the first test sample is converted to a second test sample comprising a second buffer that is compatible with a second assay. In some embodiments, the first or second assay includes an immunoassay for identification of type A or type B influenza virus in the sample. In some embodiments, the first or second assay is an assay to determine sensitivity of the influenza virus neuraminidase to a certain antiviral drug.

In some embodiments, a specimen is added to a first buffer compatible with an immunoassay for identification of type A or type B influenza virus in order to prepare an immunoassay test sample. A first portion of the immunoassay test sample can be applied to an immunoassay for identification of type A or type B influenza virus. A second portion can be converted to a neuraminidase assay test sample by contacting the immunoassay test sample to an exchange matrix equilibrated with a second buffer compatible with a neuraminidase activity assay. Examples of matrices include cross-linked polysaccharides such as sephadex and sepharose. In some embodiments, the neuraminidase comprises a cartridge comprising a chamber comprising the matrix. The sephadex variety may be a G25 medium, G25 course, G25 fine. The bed height may be anywhere from one centimeter to 15 centimeters. In some embodiments, the resin can be provided pre-washed and pre-equilibrated in a buffer that promotes the release of the influenza neuraminidase and a subsequent neuraminidase activity measurement. Such reagents are be similar to those found in the NA-STAR™ and NA-FLUOR™ Kits and the ZstatFlu™ Product. These buffers will typically contain low sodium chloride content, such as less than 100 mM and often less than 10 mM. In some embodiments, the sodium chloride content is from 100 mM and 0.1 mM, 100 mM and 1 mM, 10 mM and 0.1 mM, and 10 mM and 1 mM. These buffers will typically contain calcium and/or magnesium ions in the range of 0.1 mM to 50 mM, 1 mM to 20 mM, or and 4 mM to 10 mM, to yield the most optimal neuraminidase activity measurement. The pH of buffers used to equilibrate the resin should be between 5 and 8 to make sure the subsequent neuraminidase activity assay can work on rare strains containing pH sensitive neuraminidase, such as the lethal influenza H7N9. The flu specimen that passes through the resin cartridge may contain a small amount of detergent similar to the detergent used to release the nucleocapsid for the flu identity immunoassay. The detergents may include NP-40, bile salts, Brij-35 and the Tritons. An example of a Triton is Triton-X-100. An example of a bile salt is sodium deoxycholate. These tissue and virus lysing agents may come in liquid stocks and in other cases be available as solids. Tritons and NP 40 may be present from 0.01% to 10% v/v, or 0.5% to 3% V/V in the sample that passes through the resin cartridge. The solid detergents may be present in concentrations ranging 0.1% to 10% W/V, or 0.5% to 2% W/V.

Figure 14:
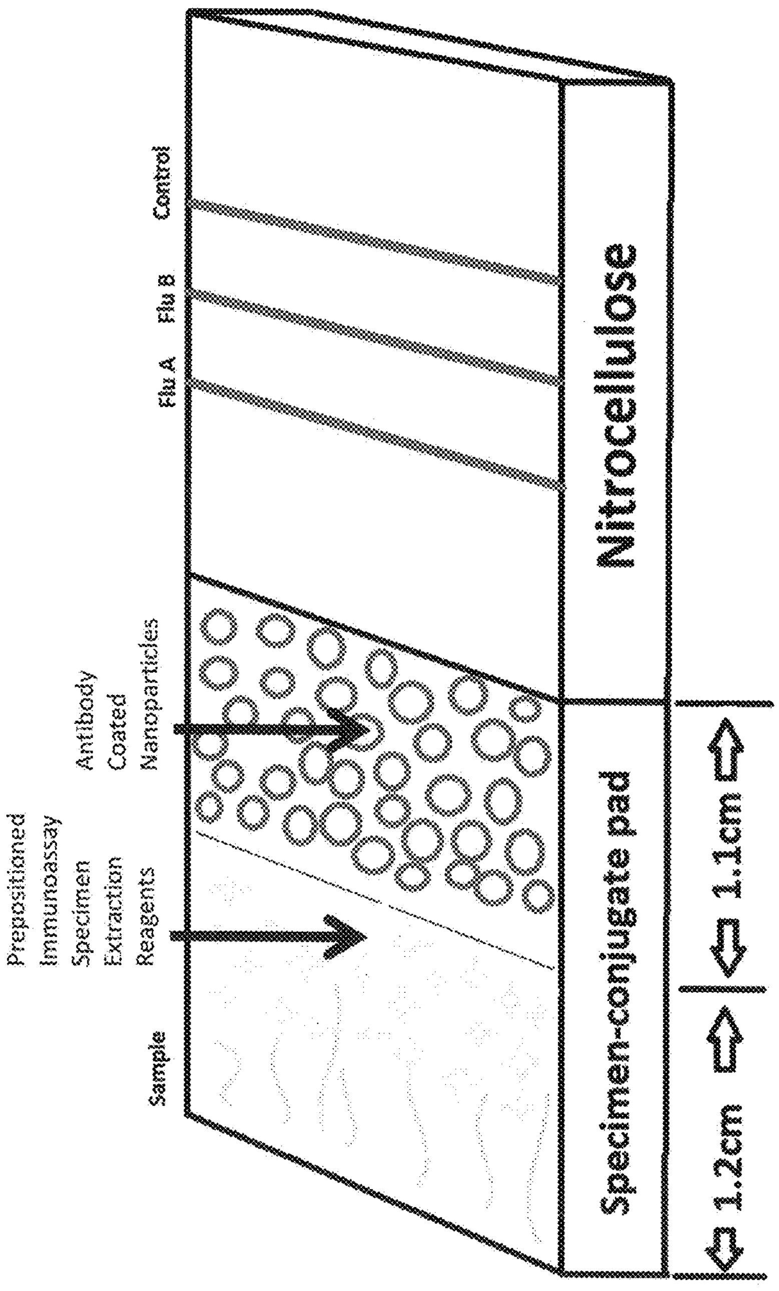
FIG. 14 depicts an embodiment of an immunoassay lateral flow test strip including prepositioning immunoassay nucleocapsid extraction reagents on the strip.

In some embodiments, a specimen is added to a first buffer compatible with a neuraminidase activity assay in order to prepare a neuraminidase assay test sample. A first portion of the neuraminidase assay test sample can be applied to a neuraminidase activity assay. A second portion can be converted to a immunoassay test sample by contacting the neuraminidase assay test sample to an exchange matrix equilibrated with a second buffer compatible with a immunoassay for identification of type A or type B influenza virus. Examples of such matrices include cross-linked polysaccharides such as sephadex, sepharose, and nitrocellulose. In some embodiments, the immunoassay comprises a test strip, and the matrix comprises nitrocellulose. In some embodiments, the second buffer is lyophilized or otherwise dried down into the matrix. The extraction buffer designed to make nucleocapsid available for immunoassay detection is prepositioned in the specimen pad the conjugate pad, or both. Suitable examples of these pads (membranes) include the glass fiber Millipore G041, Millipore GFDX and cellulosic Millipore C083, Millipore C048, Millipore C068, Millipore C083, Millipore C248, A specific family of suitable Millipore pads is the SureWick Product Line. Other suitable examples are the GE Healthcare CF1, CF3, CF4 cotton linter, Whatman Fusion 5, Std 14 and Std 15, and polyester specimen-conjugate pads are other examples. FIG. 14 illustrates an embodiment of the prepositioning of immunoassay nucleocapsid extraction reagents on the immunoassay lateral flow test strip.

Measuring Sensitivity of a Neuraminidase to a Test Compound

Some embodiments provided herein include measuring the sensitivity of a neuraminidase to a test compound. A test compound includes an antiviral drug, such as an antiviral drug to influenza. In embodiments, the activity of a neuraminidase is measured in the presence and absence of a test compound. The ratio of the activity can be used to determine an inhibition value, and the inhibition value can be compared to a selected inhibition threshold to determine whether the neuraminidase is sensitive or resistant to the test compound.

In some embodiments, an inhibition threshold value can be determined by determining the inhibition values for a panel of different viruses with known sensitivity or resistance to a particular test compound. The inhibition values for each virus can be plotted, and the inhibition threshold determined to lie between the inhibition values of viruses that are sensitive to the test compound, and the inhibition values of viruses that are resistant to the test compound. Applicants have discovered that unexpectedly, inhibition thresholds for influenza type A and influenza type B are different. In some embodiments, type A virus has a lower inhibition threshold than type B virus for certain test compounds. In some embodiments, if the type of influenza virus in a sample is known (e.g., type A or type B), the appropriate inhibition threshold level can be applied for the compound tested, which can increase the sensitivity of the assay significantly, enabling the ability to resolve flu strains with only a low level of drug resistance from those strains that show no drug resistance of any kind.

Neuraminidase Test Cartridges

Some embodiments of the methods and compositions provided herein include test cartridges for a neuraminidase assay. In some embodiments, a neuraminidase assay to determine sensitivity to a test compound, such as a test drug and/or an antiviral drug, can be performed in a cartridge comprising a matrix chamber and a reagent chamber. In some embodiments, the cartridge can include one or more test chambers. The test chambers can include one more test chambers for: specimen+assay reagents without test compound; assay reagents without specimen or test compound; specimen+assay reagents+test compound; and assay reagent+test compound without specimen. In some embodiments, multiple test compounds are tested, and additional test chambers for specimen+assay reagents+test compound, and assay reagent+test compound without specimen for each additional test compound are included (e.g. first, second, third, fourth, etc. test compound). The control test chambers for specimen+assay reagents and/or assay reagents, can be utilized for all of the test compounds tested on the cartridge. In some embodiments, the matrix chamber is in fluid communication with one or more other chamber, such as chambers that are selected to contain specimen. In some embodiments, the test chambers include: (1) Test with drug, which includes specimen, reaction mixture and test drug; (2) Test without drug, which includes specimen and reaction mixture; (3) Control for reaction mixture, which includes reaction mixture; and (4) Control for test drug, which includes reaction mixture and drug. In some embodiments, other controls may be includes.

Figure 5:
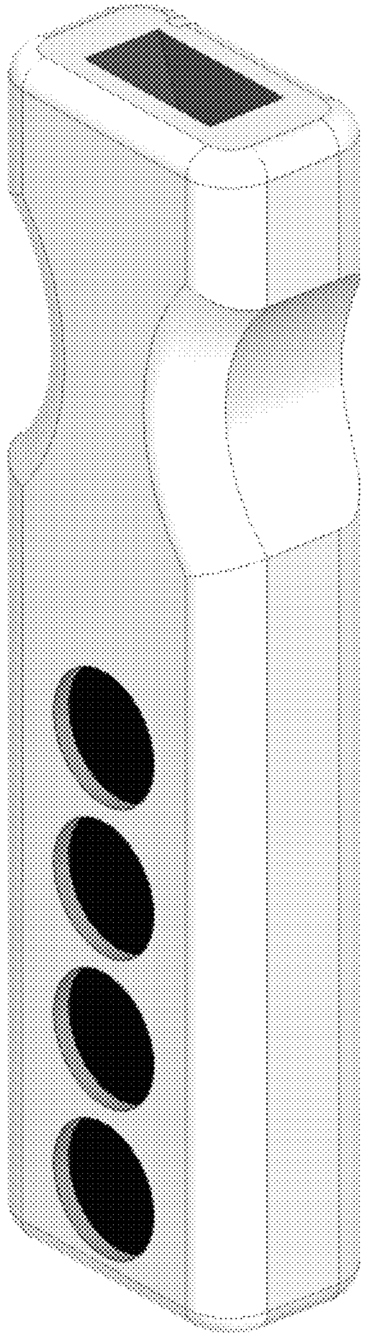
FIG. 5 depicts an embodiment of a cartridge for a kinetic flow neuraminidase assay.

In some embodiments, a fluid sample is added to the matrix chamber. The fluid sample flows through the matrix chamber to a chamber selected to contain sample by one or more forces selected from diffusion, capillary flow, and gravity. Signal from a reaction occurring in a chamber can be measured using a photomultiplier tube. An example cartridge is shown in FIG. 5.

Methods for Detecting Influenza Virus

Some embodiments provided herein include detecting an influenza virus comprising contacting a sample with an immunoassay buffer adapted for an immunoassay for detecting an influenza virus type A or an influenza virus type B, thereby obtaining an immunoassay test sample; contacting a first portion of the immunoassay test sample to a test strip comprising an immunoassay for detecting an influenza type A or type B, thereby detecting the presence or absence of influenza type A or type B in the sample; contacting a second portion of the immunoassay test sample with a matrix comprising a neuraminidase assay buffer, thereby obtaining a neuraminidase test sample; and contacting the neuraminidase test sample with a neuraminidase assay, thereby detecting the presence of a neuraminidase in the sample. In some embodiments, the immunoassay buffer is incompatible with an assay for neuraminidase activity. In some embodiments, the immunoassay buffer inhibits neuraminidase activity.

Some embodiments of the methods and compositions provided herein include methods for detecting an influenza virus comprising: contacting a sample with a neuraminidase assay buffer adapted for an neuraminidase assay, thereby obtaining a neuraminidase test sample; contacting a first portion of the neuraminidase test sample to a test strip comprising an immunoassay for detecting an influenza type A or type B, wherein the neuraminidase test sample contacts a matrix comprising immunoassay buffer, thereby obtaining an immunoassay test sample and detecting the presence or absence of influenza type A or type B in the sample; and contacting a second portion of the neuraminidase test sample with a neuraminidase assay, thereby detecting the presence of a neuraminidase in the sample. In some embodiments, the neuraminidase assay buffer is incompatible with an immunoassay for detecting an influenza type A or type B. In some embodiments, the neuraminidase assay buffer inhibits specific binding of an antibody to an antigen selected from the group consisting of influenza type A and influenza type B. In some embodiments, the matrix comprises lyophilized immunoassay buffer.

In some embodiments, the matrix comprising a neuraminidase assay buffer, and the reagents for the neuraminidase assay are in the same vessel, such as a cartridge. In some embodiments, the vessel comprises a plurality of chambers, such as a chamber comprising the matrix, and a chamber comprising reagents for the neuraminidase assay. In some embodiments, the matrix comprises a cross-linked polysaccharide, such as sephadex and sepharose. In some embodiments, the vessel comprises a multiwell cartridge adapted to be read using a photomultiplier tube, such as a portable photomultiplier tube. The multiwell strip or multiwell strip-resin cartridge is then moved across a rail positioning each well directly under the detector. Movement across the rail is done by a stepping motor which is programmed to pause and allow each well to be counted.

In some embodiments, the immunoassay test sample and the neuraminidase test sample are moved in the vessel by one or more forces selected from gravity, capillary action, and diffusion.

Some embodiments of the methods and compositions provided herein include determining the sensitivity of a neuraminidase to a test compound comprising: (a) obtaining an inhibition value ratio, wherein the ratio comprises the level of neuraminidase activity in the presence of a test compound compared to the level of neuraminidase activity in the absence of the test compound; and (b) comparing the inhibition value ratio to an inhibition threshold, thereby determining the sensitivity of the neuraminidase activity to the test compound. An inhibition value ratio above the inhibition threshold indicates that the neuraminidase activity is sensitive to the test compound, and therefore the flu strain is sensitive to the test compound, and a ratio below the threshold indicates the neuraminidase activity is not sensitive to the test compound, and therefore the flu strain is resistant to the test compound. In some embodiments, the inhibition threshold is determined by the detection of a type A or a type B virus. In some embodiments, the inhibition threshold is determined by the test compound. In some embodiments, a test compound can be selected according to the sensitivity of the neuraminidase to the test compound in order to treat the influenza. In some embodiments, a patient suffering from the flu strain tested can be advised to take the test compound, or the test compound can be provided to a patient, where the neuraminidase is sensitive to the test compound.

In some embodiments, a neuraminidase assay comprises a dual enzyme assay comprising a signaling enzyme. In some embodiments, neuraminidase activity produces a substrate for the signaling enzyme. In some embodiments, the neuraminidase assay comprises a conjugate of a N-acetylneuraminic acid and luciferin or a derivative thereof. In some embodiments, neuraminidase activity produces an inhibitor for the signaling enzyme. In some embodiments, the neuraminidase assay comprises a conjugate of a N-acetylneuraminic acid and a trifluoromethylketone or a derivative thereof. In some embodiments, the signaling enzyme comprises luciferase. In some embodiments, the immunoassay buffer inhibits luciferase activity. In some embodiments, the level of neuraminidase activity is measured using a photomultiplier tube.

In some embodiments, the test compound is an antiviral drug. In some embodiments, the test compound is an antiviral drug selected from the group consisting of Oseltamivir, Zanamivir, Peramivir and lanimivir.

In some embodiments, the immunoassay comprises a sandwich assay.

In some embodiments, the sample is obtained from a subject, such as a human, such as subject suspected of having influenza.

In some embodiments, the combination assay described herein has a limit of detection of influenza virus in terms of infectious dose of at least 2000 $TCID_{50}$/ml, 1000 $TCID_{50}$/ml, 500 $TCID_{50}$/ml, 200 $TCID_{50}$/ml, 100 $TCID_{50}$/ml, or a range defined by any two of these values. On a molar basis the disclosed combination test has the ability to detect neuraminidase at at least 1000 fM, 500 fM, 100 fM, 10 fM, or a range defined by any two of these values.

Methods for Selecting a Treatment

Some embodiments of the methods and compositions provided herein include methods for selecting a treatment for an influenza virus comprising (a) contacting a sample with an immunoassay buffer adapted for an immunoassay for detecting an influenza virus type A or an influenza virus type B, thereby obtaining an immunoassay test sample; (b) contacting a first portion of the immunoassay test sample to a lateral flow test strip comprising an immunoassay for detecting an influenza type A or type B, thereby detecting the presence or absence of influenza type A or type B in the sample; (c) contacting a second portion of the immunoassay test sample with a matrix comprising a neuraminidase assay buffer, thereby obtaining a neuraminidase test sample; (d) contacting the neuraminidase test sample with a neuraminidase assay, thereby determining the sensitivity of a neuraminidase of the neuraminidase test sample to a test compound (e.g. influenza antiviral drug), the determining comprising: (i) obtaining an inhibition value ratio, wherein the ratio comprises the level of neuraminidase activity in the presence of a test compound compared to the level of neuraminidase activity in the absence of the test compound, and (ii) comparing the inhibition value ratio to an inhibition threshold, thereby determining the sensitivity of the neuraminidase activity to the test compound; and (e) selecting or identifying the test compound determined to inhibit neuraminidase activity. In some embodiments, the inhibition threshold is determined by the detection of the type A or a type B virus. In some embodiments, the immunoassay buffer is incompatible with an assay for neuraminidase activity. In some embodiments, the immunoassay buffer inhibits neuraminidase activity. In some embodiments, steps (c) and (d) are performed in the same vessel. In some embodiments, the subject is suspected of having influenza. In some embodiments, the subject is human.

Some embodiments of the methods and compositions provided herein include methods for selecting a treatment for an influenza virus comprising: (a) contacting a sample with a neuraminidase assay buffer adapted for an neuraminidase assay, thereby obtaining a neuraminidase test sample; (b) contacting a first portion of the neuraminidase test sample to a test strip comprising an immunoassay for detecting an influenza type A or type B, wherein the neuraminidase test sample contacts a matrix comprising immunoassay buffer, thereby obtaining an immunoassay test sample and detecting the presence or absence of influenza type A or type B in the sample; and (c) contacting a second portion of the neuraminidase test sample with a neuraminidase assay, thereby determining the sensitivity of a neuraminidase of the neuraminidase test sample to a test compound, the determining comprising: (i) obtaining an inhibition value ratio, wherein the ratio comprises the level of neuraminidase activity in the presence of a test compound compared to the level of neuraminidase activity in the absence of the test compound, and (ii) comparing the inhibition value ratio to an inhibition threshold, thereby determining the sensitivity of the neuraminidase activity to the test compound; and (e) selecting the test compound determined to inhibit neuraminidase activity. In some embodiments, the inhibition threshold is determined by the detection of the type A or a type B virus. In some embodiments, the matrix comprises lyophilized immunoassay buffer. In some embodiments, step (c) is performed in the same vessel.

In some embodiments, the inhibition threshold is determined by the detection of the type A or a type B virus, wherein a first inhibition threshold is used if type A flu virus is detected, and a second inhibition threshold is used if type B flu virus is detected. In some embodiments, the inhibition threshold is lower if type A flu virus is detected than if type B flu virus is detected.

In some embodiments, the vessel comprises a plurality of chambers, such as a chamber comprising the matrix, and a chamber comprising reagents for the neuraminidase assay. In some embodiments, the matrix comprises a cross-linked polysaccharide, such as sephadex and sepharose.

In some embodiments, the vessel comprises a cartridge, such as a multiwell cartridge adapted to be read using a photomultiplier tube. In some embodiments, the photomultiplier tube is portable.

In some embodiments, the neuraminidase assay comprises a dual enzyme assay comprising a signaling enzyme. In some embodiments, neuraminidase activity produces a substrate for the signaling enzyme. In some embodiments, the neuraminidase assay comprises a conjugate of a N-acetylneuraminic acid and luciferin or a derivative thereof. In some embodiments, neuraminidase activity produces an inhibitor for the signaling enzyme. In some embodiments, the neuraminidase assay comprises a conjugate of a N-acetylneuraminic acid and a trifluoromethylketone or a derivative thereof. In some embodiments, the signaling enzyme comprises luciferase. In some embodiments, the level of neuraminidase activity is measured using a photomultiplier tube.

In some embodiments, the test compound is an antiviral drug. In some embodiments, the test compound is an antiviral drug selected from the group consisting of Oseltamivir, Zanamivir, Peramivir and Lanamivir.

In some embodiments, the immunoassay comprises a sandwich assay.

In some embodiments, the sample is obtained from a subject.

Systems and Kits

Some embodiments provide herein include diagnostic systems for detecting influenza virus. In some embodiments, such systems include a cartridge for determining neuraminidase activity in a sample, wherein the cartridge is configured to process a sample comprising an incompatible buffer for the determination to a sample comprising a compatible buffer for the determination; and a test strip for detecting influenza type A or type B in the sample, wherein the test strip, such as a lateral flow strip, is configured to process a sample comprising an incompatible buffer for the detection to a sample comprising a compatible buffer for the detection. In some embodiments, such systems also include a first detector configured to measure a signal from the cartridge; and a second detector configured to measure a signal from the test strip.

In some embodiments, the cartridge comprises a matrix chamber comprising a cartridge matrix comprising the compatible buffer for the determination, and a reagent chamber comprising reagents for the neuraminidase activity determination. In some embodiments, the cartridge matrix comprises a cross-linked polysaccharide. In some embodiments, the cartridge matrix is selected from the group consisting of sephadex and sepharose. In some embodiments, the matrix chamber and cartridge chamber are in fluid communication such that a sample applied to the matrix chamber flows from the matrix chamber to the reagent chamber. In some embodiments, the sample flows in the cartridge by one or more forces selected from gravity, capillary action, and diffusion. In some embodiments, the cartridge comprises a multiwell cartridge adapted to be read using a photomultiplier tube.

In some embodiments, the test strip comprises an immunoassay. In some embodiments, the immunoassay is a sandwich assay. In some embodiments, the test strip comprises a matrix comprising the compatible buffer for the detection. In some embodiments, the matrix comprises nitrocellulose. In some embodiments, the compatible buffer for the detection is lyophilized.

In some embodiments, the first detector comprises a luminometer. In some embodiments, the first detector comprises a reflectance reader. In some embodiments, the second detector comprises a photomultiplier tube. In some embodiments, a device comprises the first and second detectors. In some embodiments, the first and second detectors are the same. In some embodiments, the device is portable. In some embodiments, the device is handheld. In some embodiments, the lateral flow strip and multiwell strip/resin cartridge are read on a common platform with two separate detection modalities, but sharing a common power source and display for reviewing the results of both ID and AST.

Some embodiments provide herein include diagnostic kits for detecting influenza virus. In some embodiments, such kits include a cartridge for determining neuraminidase activity in a sample, wherein the cartridge is configured to process a sample comprising an incompatible buffer for the determination to a sample comprising a compatible buffer for the determination; and a test strip for detecting influenza type A or type B in the sample, wherein the test strip is configured to process a sample comprising an incompatible buffer for the detection to a sample comprising a compatible buffer for the detection.

Some embodiments also include a first detector configured to measure a signal from the cartridge; and a second detector configured to measure a signal from the test strip.

Some embodiments also include reagents for a neuraminidase activity assay. In some embodiments, the neuraminidase activity assay reagents are selected from the group consisting of luciferase, a conjugate of a N-acetylneuraminic acid and luciferin or a derivative thereof, a N-acetylneuraminic acid and a trifluoromethylketone or a derivative thereof, and an antiviral drug. In some embodiments, the antiviral drug is selected from the group consisting of Oseltamivir, Zanamivir, Peramivir and Lanamivir.

Some embodiments also include reagents for an immunoassay. In some embodiments, the immunoassay reagents are selected from the group consisting of an antibody specific to an influenza type A antigen, and an antibody specific to an influenza type B antigen.

EXAMPLES

Example 1—Combination Assay

This example illustrates an example workflow with an influenza type A or type B test, and a neuraminidase drug resistance test. A kit comprising: an applicator tube containing an immunoassay extraction buffer and a lid with an opening; a first test device comprising a lateral flow immunoassay to identify influenza type A or type B; and a second test device comprising a kinetic flow assay to determine neuraminidase drug resistance, is unwrapped from packaging and each component labeled with a patient's identification. A specimen is collected from a patient's nose using a swab. The swab is inserted into the extraction buffer and swirled against the inside wall three times. The swab is removed from the extraction buffer while squeezing the sides of the tube, and then discarded. The lid of the applicator tube is attached to the tube.

The applicator tube is inverted and three drops (~85 μl) of the extraction buffer are squeezed through the lid and applied to the first test device. The first test device includes a specimen pad non-overlapping with detector reagents that contains a first test buffer for the first test. The specimen diffuses through the first test buffer into the test site of the first test device. The first test device is incubated for 10 minutes, and the results of the first test are measured using a reader. The reader provides an indication whether type A or type B influenza virus is present in the sample.

The applicator tube is inverted and the remaining extraction buffer is squeezed through the lid and applied to the second test device. In this test, an increase in neuraminidase results in an increase in luciferase signal. The second device includes a buffer exchange chamber (aka matrix chamber) and reaction chambers. The specimen diffuses through the buffer exchange chamber to the reaction chambers for the neuraminidase drug resistance assays. An inhibition value is the ratio of signal with test drug to signal without test drug, taking into account background levels of signal produced by reaction mixture and test drug. The reaction chambers are shown in TABLE 5A.

TABLE 5A

| Reaction chamber | Description | Contents of chamber |
| --- | --- | --- |
| 1 | test without drug | reaction mixture + specimen |
| 2 | test with drug | reaction mixture + specimen + test antiviral drug |
| 3 | control for reaction mixture | reaction mixture |
| 4 | control for reaction mixture and test drug | reaction mixture + test antiviral drug |

The second test device is incubated and the signals from each chamber measured using a photomultiplier tube. An inhibition value is determined using the following formula from the signals from each reaction chamber:

$$\text{Inhibition value} = \frac{(\text{test with drug}) - (\text{control for drug})}{(\text{test without drug}) - (\text{control for reaction mix})} \times \text{amplifier}$$

The drug sensitivity threshold levels for each test antiviral drug are selected according to the influenza type determined in the first test, and the test antiviral drug used. If the inhibition value is below the inhibition threshold value, the neuraminidase is determined to be sensitive to the test antiviral drug.

Example 2—Sensitivity of Photomultiplier Tube Apparatus

Figure 6:
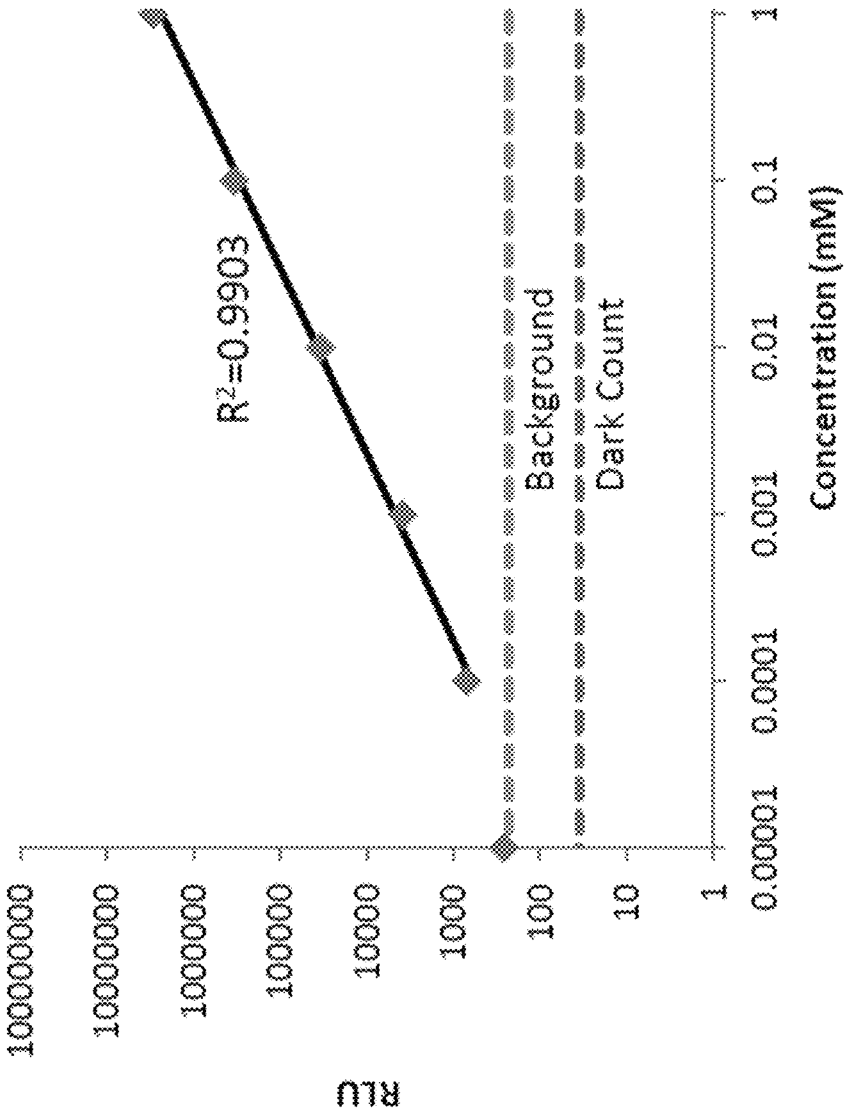
FIG. 6 is a graph of relative light units and concentration of a fluorescent control measured using a portable reader.

This example demonstrates the sensitivity of a Hamamatsu TO-Can photomultiplier tube device and the ability to carry out the low dark noise reading in a portable handheld system. Relative light units (RLU) were measured for various concentrations of a positive chemiluminescent signal producing control reagent (Cell Titer Glo) using a Hamamatsu TO-Can photomultiplier tube device. Controls included a background control and a dark count control. The results are shown in FIG. 6.

Example 3—Dual Enzyme Assay

Figure 7:
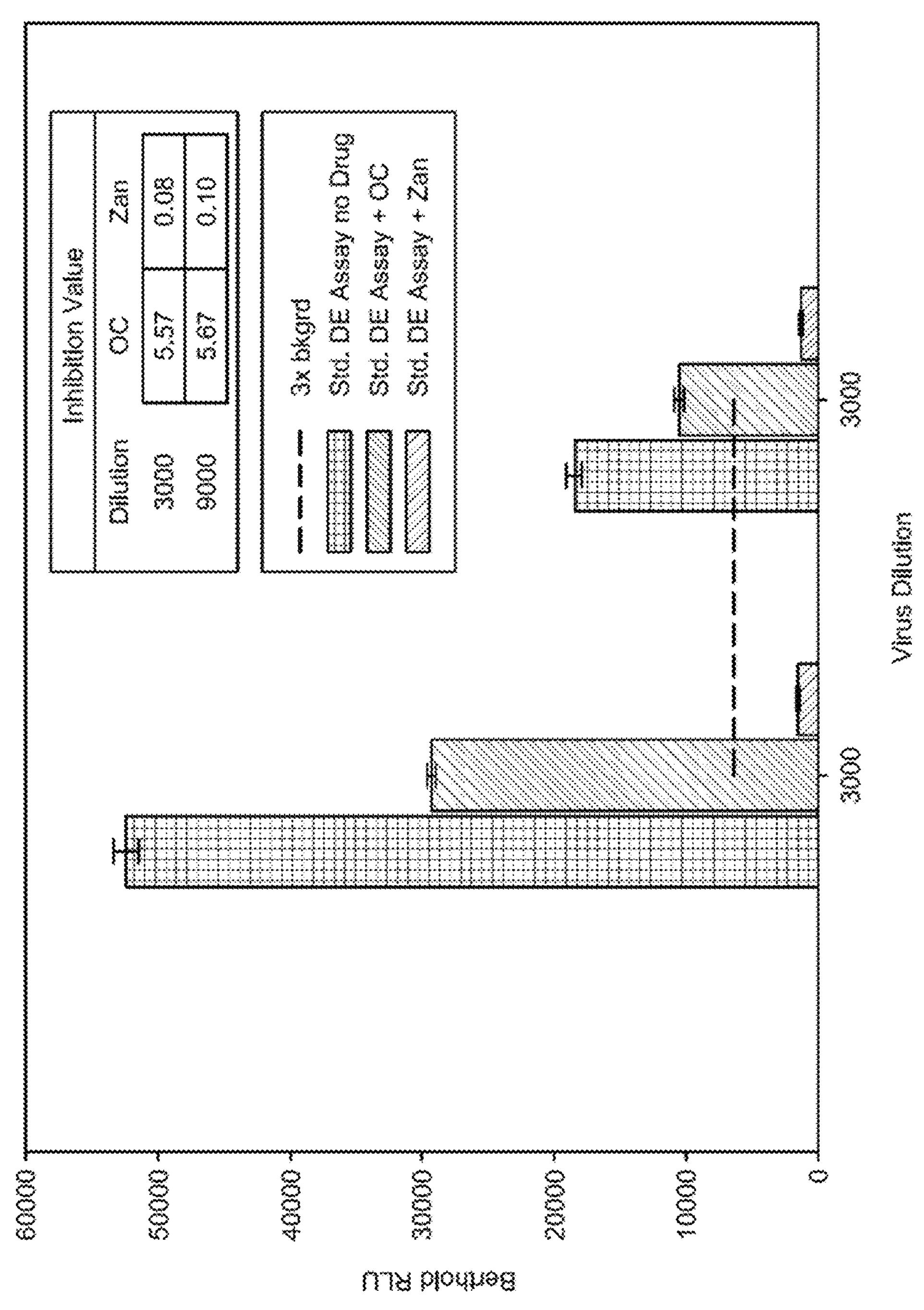
FIG. 7 is a graph of relative light units for neuraminidase assays, and demonstrates the ability of a Dual Enzyme Assay to select the best NA-based antiviral for treatment. In the example, Relenza outperforms Tamiflu.

This example demonstrates a dual enzyme assay for the test strain A/Mississippi/03/2001 A(H1N1) H275Y which comprises a neuraminidase that is sensitive to Zanamivir and resistant to Oseltamivir. Specimen comprising the test strain was diluted 1/3000 or 1/9000 and applied to a kinetic flow test device. Test chambers in the kinetic flow test assay included those as in TABLE 5A, that is: (1) reaction mixture+specimen; (2) reaction mixture+specimen+test antiviral drug; (3) control:reaction mixture; and (4) control:reaction mixture+test antiviral drug. Signal from each test chamber was measured using a photomultiplier tube device. The results are shown in FIG. 7. The assay showed that the test strain was more sensitive to Zanamivir than Oseltamivir.

Example 4—Sensitivity of Various Influenza A Strains

Figure 8:
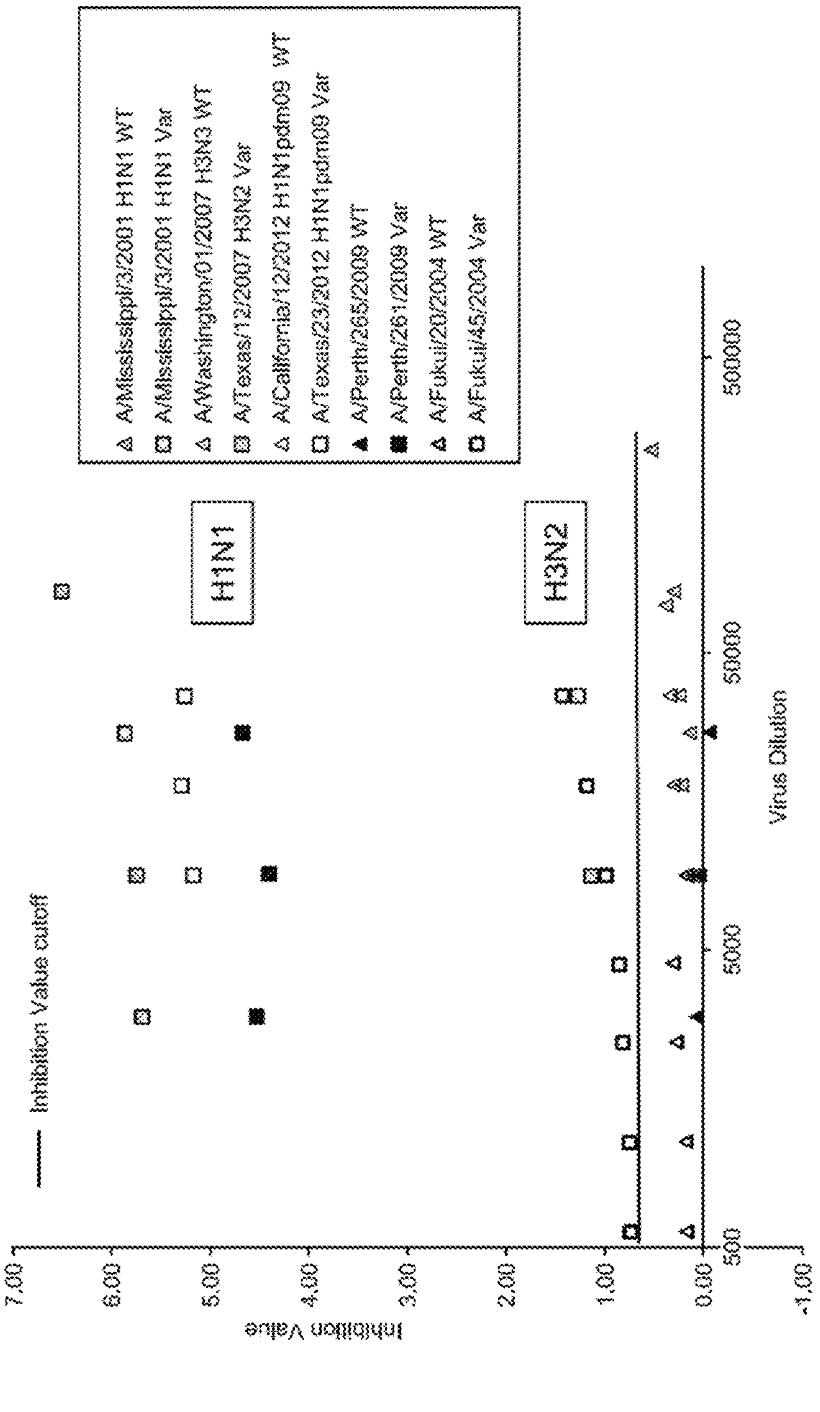
FIG. 8 is a graph of inhibition values for various dilutions of various type A influenza viruses, and demonstrates that there is a distinct inhibition value that can be used to discern Flu A drug resistant from Flu A drug sensitive strains, which is distinct from the value for Flu B strains, and BD has the ability to make the judgment in a POC setting, when the AST test follows a conventional Flu ID test which provides A/B typing.

This example demonstrates determining an inhibition threshold level for a panel of type A influenza viruses of known sensitivity or resistance to Oseltamivir. Specimens were prepared from various dilutions of various influenza A strains, and applied to a kinetic flow test device with Oseltamivir. Test chambers on the kinetic flow assay included those as in TABLE 5A, that is: (1) reaction mixture+specimen; (2) reaction mixture+specimen+test antiviral drug; (3) control:reaction mixture; and (4) control:reaction mixture+test antiviral drug. Signal from each test chamber was measured using a photomultiplier tube. An inhibition value for each strain was determined as in Example 1. Inhibition values were plotted on a graph for various dilutions of each strain, and a threshold inhibition value was determined from the graph. The threshold inhibition value, or cutoff value, to discern drug sensitive from drug resistant was about 0.6. The cut off was determined to be a value where error bars from the drug sensitive strains did not overlap with the flu resistant strains. See FIG. 8.

Example 5—Sensitivity of Various Influenza B Strains

Figure 9:
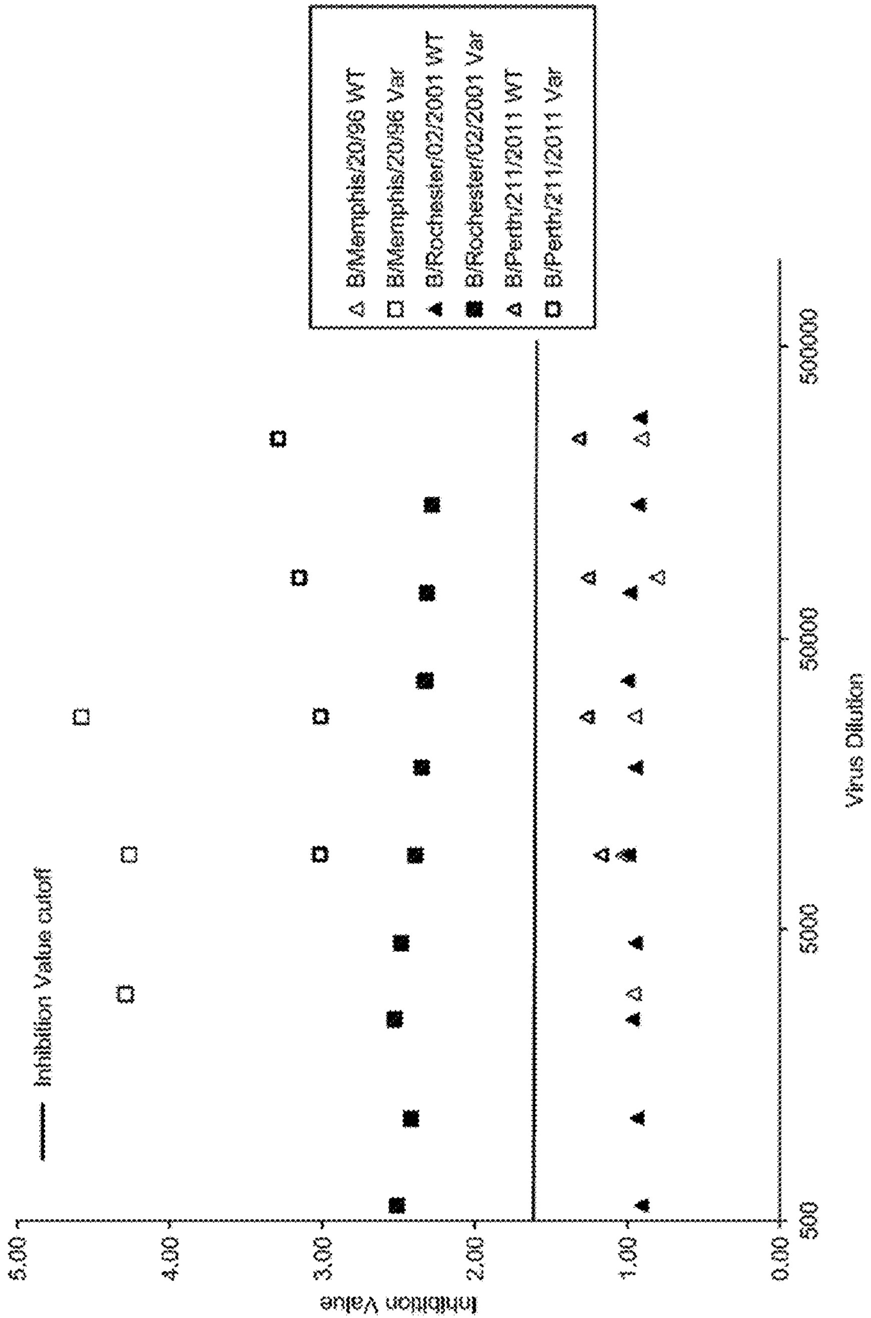
FIG. 9 is a graph of inhibition values for various dilutions of various type B influenza viruses, and demonstrates that there is a distinct inhibition value that can be used to discern Flu B drug resistant from Flu B drug sensitive strains, which is distinct from the value for Flu A strains, and BD has the ability to make the judgment in a POC setting, when the AST test follows a conventional Flu ID test which provides A/B typing.

This example demonstrates determining an inhibition threshold level for a panel of type A influenza viruses of known sensitivity or resistance to Oseltamivir. Specimens were prepared and tested as in Example 4. An inhibition value for each strain was determined. Inhibition values were plotted on a graph for various dilutions of each strain, and a threshold inhibition value was determined from the graph. The threshold inhibition value, or cutoff value, to discern drug sensitive from drug resistant is about 1.55. See FIG. 9.

Example 6—Effect of Buffer Exchange on Lateral Flow Assay

This example demonstrates the sensitivity of the lateral flow immunoassay to determine influenza type A or type B in a specimen, after buffer exchange from kinetic flow neuraminidase assay buffer. Specimens of various dilutions of influenza viruses: A/PR/8/34, B/Florida/4/2006, and A/Texas/12/2007, were tested using (1) the lateral flow Veritor™ assay according to the package insert, or (2) the lateral flow Veritor™ assay with buffer exchange from kinetic flow assay extraction buffer to immunoassay extraction buffer present in the lateral flow pad. Signals were measured and the reader provided a determination of the presence of absence of influenza type A and/or type B in each sample. TABLE 6 summarizes the results. Notably, influenza type A or type B were identified in more dilute specimens in assays using a protocol with Veritor™ with buffer exchange, than with Veritor™ assay according to the package insert.

TABLE 6

| | Veritor ™ | | | | Veritor ™ with buffer exchange | | | |
|---|---|---|---|---|---|---|---|---|
| | | Reader Output | | Raw Reflectance | | Reader Output | | Raw Reflectance |
| Virus | Dilution | Flu A | Flu B | Data | Dilution | Flu A | Flu B | Data |
| A/PR/8/34 | 2,500:1 | + | − | 5.92 | 2,500:1 | + | − | 6.9 |
| | 5,000:1 | + | − | 3.04 | 5,000:1 | + | − | 4.3 |
| | 10,000:1 | − | − | 1.54 | 10,000:1 | + | − | 2.23 |
| | 20,000:1 | − | − | 0.95 | 20,000:1 | − | − | 0.86 |
| B/Florida/4/2006 | 100:1 | − | + | 8.57 | 100:1 | − | + | 11.31 |
| | 200:1 | − | + | 3.31 | 200:1 | − | + | 5.52 |
| | 400:1 | − | − | 1.4 | 400:1 | − | + | 2.77 |
| | 800:1 | − | − | 0.67 | 800:1 | − | − | 0.94 |
| A/Texas/12/2007 | 10000:1 | + | − | 5.6 | 10000:1 | + | − | 14.97 |
| | 20000:1 | + | − | 3.06 | 20000:1 | + | − | 8.1 |
| | 40000:1 | − | − | 1.38 | 40000:1 | + | − | 4.19 |
| | 80000:1 | − | − | 0.48 | 80000:1 | − | − | 1.67 |

Example 7—Sensitivity of Immunoassay and Dual Enzyme (DE) Assay

The Veritor immunoassay and the dual enzyme neuraminidase kinetic flow assay with Oseltamivir were performed on various dilutions of the influenza virus: A/Perth/211/2001 WT. TABLE 7 summarizes the results for two experiments. These results demonstrate that applying a specimen in immunoassay extraction buffer to a G25M sephadex resin pre-equilibrated with neuraminidase activity buffer did not have a negative effect on the sensitivity of the standard (Std) DE Assay. The Std DE Assay was able to provide a drug sensitivity result at clinically relevant specimen concentrations.

TABLE 7

| Specimen dilution | Veritor result | Dual enzyme assay result from cartridge processed specimen | Inhibition value |
|---|---|---|---|
| 1:250 | +/+ | ND | ND |
| 1:500 | +/+ | ND | ND |
| 1:1K | +/− | ND | ND |
| 1:3K | −/− | +/+ | 1.48/1.34 |

ND: not determined

Example 8—Detecting Drug Resistance in Mixed Influenza Specimens

Figure 10:
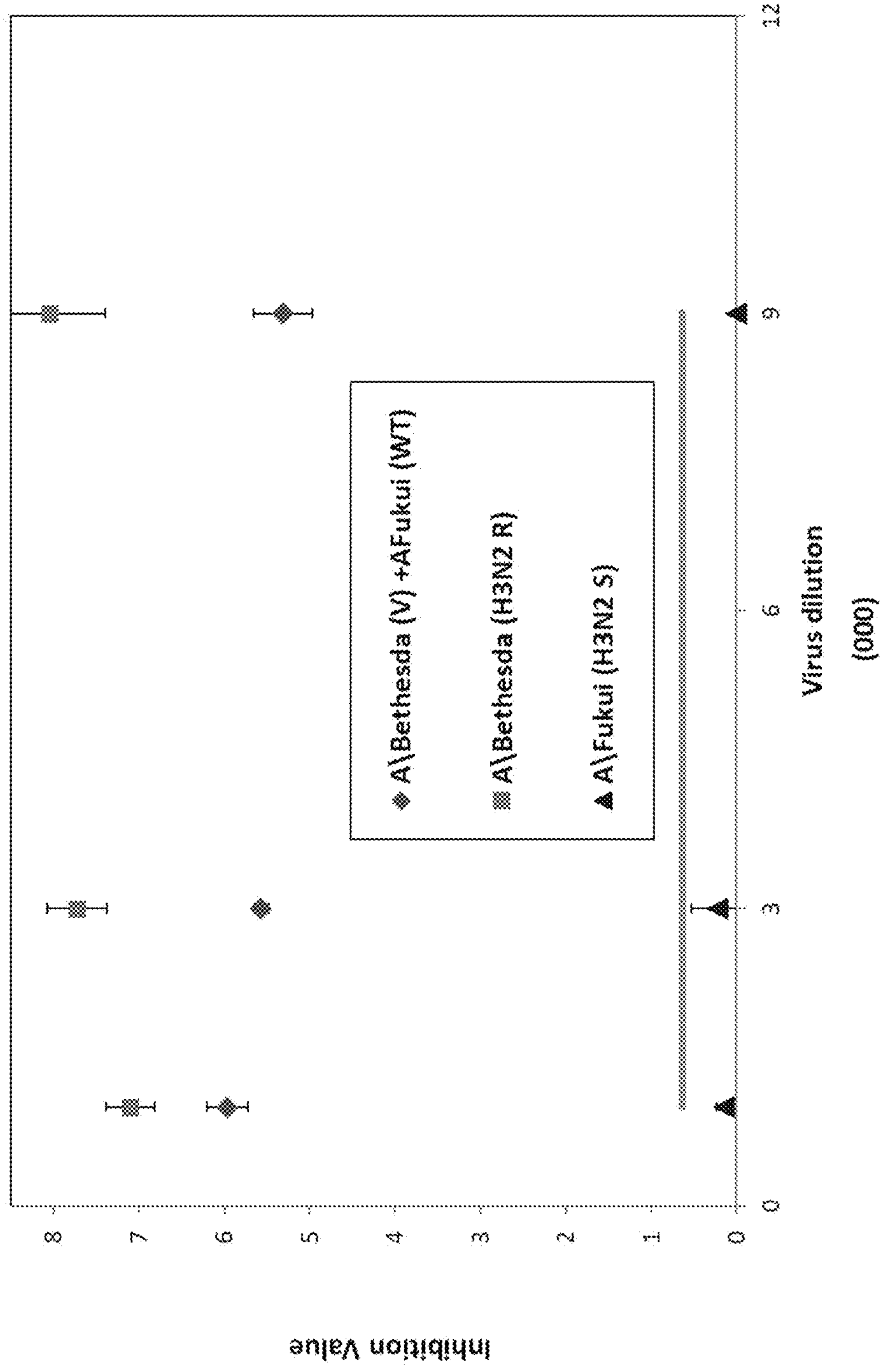
FIG. 10 is a graph of inhibition values for various dilutions of mixtures of viruses, and demonstrates the ability of the technology described herein to flag the presence of drug resistant strains when they exist in mixed cultures. Even more significant is the ability demonstrated to flag highly drug resistant influenza possessing the pH sensitive NA.

Various dilutions of specimens were assayed using a kinetic flow assay with the antiviral drug, Oseltamivir. Specimens included A\Bethesda (H3N2 R); A\Fukui (H3N2 S); and the mixture A\Bethesda (V)+AFukui (WT). Signals were measured using a photomultiplier tube, and inhibition values determined. The results are summarized in FIG. 10. These results demonstrate that the Std Dual Enzyme AST Detection Chemistry, when following an assay that distinguishes Flu A from Flu B (allowing the most appropriate inhibition value to be applied), using a PMT with single photon detection and applying background subtraction can identify a drug resistant strain when present in a specimen with a drug sensitive strain.

Example 9—Comparison of Dual Enzyme Assays

Figure 11:
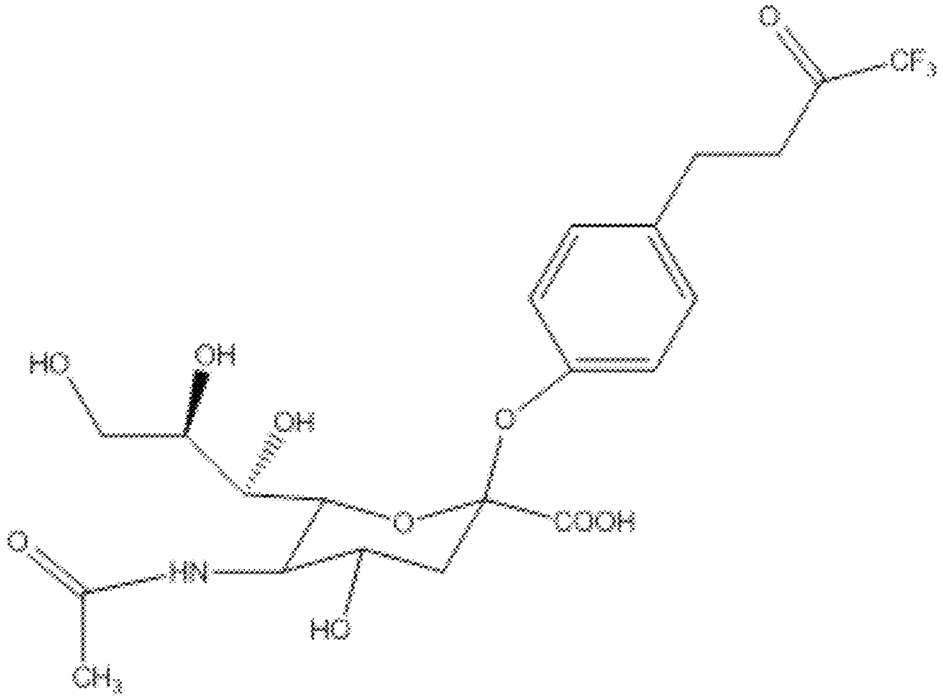
FIG. 11 shows the chemical structure of an exemplary neuraminidase substrate, NANA-CF3 (masked inhibitor) and the trifluoroketone (free inhibitor), used in an embodiment of a dual enzyme cascade for antiviral susceptibility testing.
Figure 11:
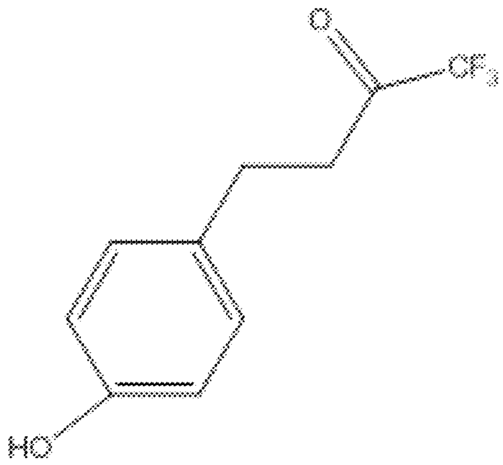
Figure 13:
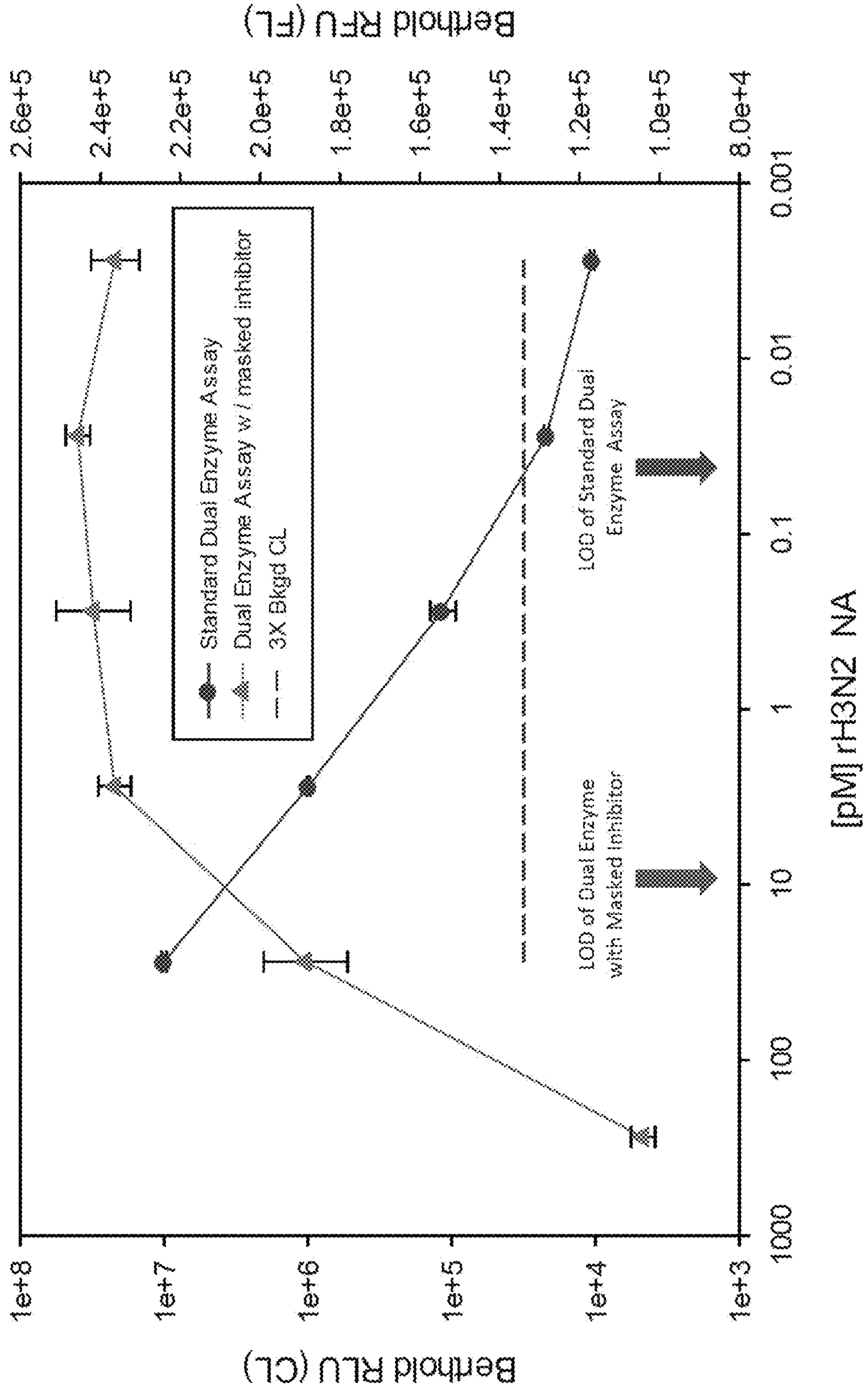
FIG. 13 is a graph of two different dual enzyme assays, and demonstrates the range of sensitivity which can be accomplished with a Dual Enzyme Detection Chemistry.

This example compares the sensitivity of two types of dual enzyme assays. Various dilutions of a purified influenza H3N2 neuraminidase were assayed with a dual enzyme assay that included either (1) a neuraminidase substrate that is precursor inhibitor for luciferase (NANA-CF3; see FIG. 11); and (2) a neuraminidase substrate that is a precursor substrate for luciferase (a conjugate of N-acetylneuraminic acid and luciferin). Neuraminidase activity cleaves NANA-CF3 to the esterase inhibitor, CFC. In an assay where the esterase comprises luciferase, neuraminidase activity results in the presence of the CFC inhibitor, which inhibits luciferase activity which results in a decrease in the conversion of a luciferase substrate to a luminescent product. See FIG. 12. The results of the assays are shown in FIG. 13. The level of detection (LOD) for assay (1, Dual Enzyme Assay w/masked inhibitor) was about 10 pM. In contrast, the level of detection for assay (2, Standard Dual Enzyme Assay) was less than 0.1 pM.

Example 10—Effect of Controlling for Background Signals

This example demonstrates the effect of subtracting background levels as described in the formula in Example 1 in calculating inhibition values of neuraminidase activity in the presence of antiviral drug. Inhibition values were determined for various concentrations of a particular strain of virus with a particular antiviral drug as in Example 1, The inhibition value without background subtractions were determined using the following formula for the signal from a chamber containing reaction mixture+specimen+test antiviral drug (test with drug), and reaction mixture+specimen (test without drug):

$$\text{Inhibition value} = \frac{\text{(test with drug)}}{\text{(test without drug)}} \times \text{amplifier}$$

The results are shown in TABLE 8. In TABLE 8, columns from left to right are results from decreasing concentration of virus. Subtracting background levels as shown in Example 1 in the calculation of inhibition values increases the sensitivity of the assay.

TABLE 8

| | Inhibition values | | | | | | | | | | |
|---|---|---|---|---|---|---|---|---|---|---|---|
| without bkgd subtraction | 0.92 | 0.95 | 0.98 | 0.99 | 1.09 | 1.13 | 1.36 | 1.70 | 2.31 | 3.41 | 5.04 |
| with bkgd subtraction | 0.91 | 0.94 | 0.96 | 0.94 | 0.99 | 0.95 | 1.00 | 0.98 | 0.93 | 0.92 | 0.92 |

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications can become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A diagnostic system for detecting influenza virus comprising:

a test for detecting influenza type A or type B in a sample, wherein the test is configured to process a sample comprising a first buffer compatible with the influenza type A or type B detection;

a cartridge for determining neuraminidase activity in the sample, wherein the cartridge is configured to process a sample comprising the first buffer into a sample comprising a second buffer, wherein the first buffer inhibits neuraminidase activity and is incompatible with the neuramidase determination, and wherein the second buffer is compatible with the neuraminidase determination; and a first detector configured to measure a signal from the test and/or the cartridge.

2. The system of claim 1, wherein the cartridge comprises neuraminidase activity assay reagents selected from the group consisting of luciferase, a conjugate of a N-acetylneuraminic acid and luciferin, a derivative of a N-acetylneuraminic acid and luciferin conjugate, an antiviral drug, and a reagent comprising a masked inhibitor compound for use in a dual enzyme influenza neuraminidase sensitivity assay.

3. The system of claim 2, wherein the masked inhibitor is selected from the group consisting of 1,1,1-Trifluro-4-(4-hydroxyphenyl)butan-2-one (para), 1,1,1-Trifluro-4-(3-hydroxyphenyl)butan-2-one (meta), and 1,1,1-Trifluro-4-(2-hydroxyphenyl)butan-2-one (ortho).

4. The system of claim 1, wherein the cartridge comprises a matrix chamber comprising a cartridge matrix comprising the second buffer for the determination, and a reagent chamber comprising reagents for the neuraminidase activity determination.

5. The system of claim 4, wherein the cartridge matrix comprises a cross-linked polysaccharide.

6. The system of claim 4, wherein the matrix chamber and reagent chamber are in fluid communication such that a sample applied to the matrix chamber flows from the matrix chamber to the reagent chamber.

7. The system of claim 1, wherein the cartridge comprises a multiwell cartridge adapted to be read using a photomultiplier tube or micro-photomultiplier tube.

8. The system of claim 1, wherein the test comprises an immunoassay.

9. The system of claim 1, wherein the immunoassay is a sandwich assay.

10. The system of claim 1, wherein the test comprises a test matrix comprising the first buffer for the detection.

11. The system of claim 10, wherein the test matrix comprises nitrocellulose.

12. The system of claim 1, wherein the first buffer for the detection is lyophilized or dried down.

13. The system of claim 1, wherein the first detector is configured to measure a signal from the test, and the system further comprises a second detector configured to measure a signal from the cartridge.

14. The system of claim 13, wherein the first detector comprises a luminometer, and the second detector comprises a photomultiplier tube or micro-photomultiplier tube.

15. A kit for detecting influenza virus comprising:

a test for detecting influenza type A or type B in a sample, wherein the test is configured to process a sample comprising a first buffer compatible with the influenza type A or type B detection; and a cartridge for determining neuraminidase activity in a sample, wherein the cartridge is configured to process a sample comprising an incompatible buffer for the determination to a sample comprising a compatible buffer for the determination, wherein the first buffer inhibits neuraminidase activity and is incompatible with the neuramidase determination, and wherein the second buffer is compatible with the neuraminidase determination.

16. The kit of claim 15, further comprising reagents for a neuraminidase activity assay.

17. The kit of claim 16, wherein the neuraminidase activity assay reagents are selected from the group consisting of luciferase, a conjugate of a N-acetylneuraminic acid and luciferin, a derivative of a N-acetylneuraminic acid and luciferin, a N-acetylneuraminic acid and a trifluoromethylketone, a derivative of a conjugate of a N-acetylneuraminic acid and a trifluoromethylketone, an antiviral drug, and a reagent comprising a masked inhibitor compound for use in a dual enzyme influenza neuraminidase sensitivity assay.

18. The kit of claim 17, wherein the masked inhibitor is selected from the group consisting of 1,1,1-Trifluro-4-(4-hydroxyphenyl)butan-2-one (para), 1,1,1-Trifluro-4-(3-hydroxyphenyl)butan-2-one (meta), and 1,1,1-Trifluro-4-(2-hydroxyphenyl)butan-2-one (ortho).

19. The kit of claim 17, wherein the antiviral drug is selected from the group consisting of Oseltamivir, Zanamivir, Lanamivir, and Peramivir.

20. The kit of claim 15, further comprising reagents for an immunoassay.

21. The kit of claim 20, wherein the immunoassay reagents are selected from the group consisting of an antibody specific to an influenza type A antigen, and an antibody specific to an influenza type B antigen.

22. A diagnostic system for detecting influenza virus comprising:

a cartridge for determining neuraminidase activity in a sample comprising a first buffer compatible with the neuraminidase determination;

a test for detecting influenza type A or type B in the sample, wherein the test is configured to process a sample comprising the first buffer into a sample comprising a second buffer, wherein the first buffer is incompatible with the test for detecting influenza type A or type B, and wherein the second buffer is compatible with the test for detecting influenza type A or type B; and a first detector configured to measure a signal from the cartridge and/or the test.

23. The system of claim 22, wherein the cartridge comprises neuraminidase activity assay reagents selected from the group consisting of luciferase, a conjugate of a N-acetylneuraminic acid and luciferin, a derivative of a N-acetylneuraminic acid and luciferin conjugate, an antiviral drug, and a reagent comprising a masked inhibitor compound for use in a dual enzyme influenza neuraminidase sensitivity assay.

24. The system of claim 23, wherein the masked inhibitor is selected from the group consisting of 1,1,1-Trifluro-4-(4-hydroxyphenyl)butan-2-one (para), 1,1,1-Trifluro-4-(3-hydroxyphenyl)butan-2-one (meta), and 1,1,1-Trifluro-4-(2-hydroxyphenyl)butan-2-one (ortho).

25. The system of claim 22, wherein the cartridge comprises a matrix chamber comprising a cartridge matrix comprising the first buffer for the determination, and a reagent chamber comprising reagents for the neuraminidase activity determination.

26. The system of claim 25, wherein the cartridge matrix comprises a cross-linked polysaccharide.

27. The system of claim 25, wherein the matrix chamber and reagent chamber are in fluid communication such that a sample applied to the matrix chamber flows from the matrix chamber to the reagent chamber.

28. The system of claim 22, wherein the cartridge comprises a multiwell cartridge adapted to be read using a photomultiplier tube or micro-photomultiplier tube.

29. The system of claim 22, wherein the test comprises an immunoassay.

30. The system of claim 22, wherein the immunoassay is a sandwich assay.

31. The system of claim 22, wherein the test comprises a test matrix comprising the second buffer for the detection.

32. The system of claim 31, wherein the test matrix comprises nitrocellulose.

33. The system of claim 22, wherein the second buffer for the detection is lyophilized or dried down.

34. The system of claim 22, wherein the first detector is configured to measure a signal from the cartridge, and the system further comprises a second detector configured to measure a signal from the test.

35. The system of claim 34, wherein the first detector comprises a photomultiplier tube or micro-photomultiplier tube, and the second detector comprises a luminometer.

36. A kit for detecting influenza virus comprising:

a cartridge for determining neuraminidase activity in a sample comprising a first buffer; and a test for detecting influenza type A or type B in the sample, wherein the test is configured to process a sample comprising the first buffer into a sample comprising the second buffer, wherein the first buffer is incompatible with the test for detecting influenza type A or type B, and wherein the second buffer is compatible with the test for detecting influenza type A or type B.

37. The kit of claim 36, further comprising reagents for a neuraminidase activity assay.

38. The kit of claim 37, wherein the neuraminidase activity assay reagents are selected from the group consisting of luciferase, a conjugate of a N-acetylneuraminic acid and luciferin, a derivative of a N-acetylneuraminic acid and luciferin, a N-acetylneuraminic acid and a trifluoromethylketone, a derivative of a conjugate of a N-acetylneuraminic acid and a trifluoromethylketone, an antiviral drug, and a reagent comprising a masked inhibitor compound for use in a dual enzyme influenza neuraminidase sensitivity assay.

39. The kit of claim 38, wherein the masked inhibitor is selected from the group consisting of 1,1,1-Trifluro-4-(4-hydroxyphenyl)butan-2-one (para), 1,1,1-Trifluro-4-(3-hydroxyphenyl)butan-2-one (meta), and 1,1,1-Trifluro-4-(2-hydroxyphenyl)butan-2-one (ortho).

40. The kit of claim 38, wherein the antiviral drug is selected from the group consisting of Oseltamivir, Zanamivir, Lanamivir, and Peramivir.

41. The kit of claim 36, further comprising reagents for an immunoassay.

42. The kit of claim 41, wherein the immunoassay reagents are selected from the group consisting of an antibody specific to an influenza type A antigen, and an antibody specific to an influenza type B antigen.

* * * * *

UNITED STATES PATENT AND TRADEMARK OFFICE

CERTIFICATE OF CORRECTION

PATENT NO. : 11,209,433 B2
APPLICATION NO. : 16/384020
DATED : December 28, 2021
INVENTOR(S) : Campbell et al.

It is certified that error appears in the above-identified patent and that said Letters Patent is hereby corrected as shown below:

In the Specification

In Column 3, Line 56, delete “Lanamivir,” and insert --Laninamivir,--.

In Column 5, Line 24, delete “Lanamivir,” and insert --Laninamivir,--.

In Column 5, Line 67, delete “assay In” and insert --assay. In--.

In Column 6, Line 34 (Approx.), delete “Lanamivir,” and insert --Laninamivir,--.

In Column 7, Line 62 (Approx.), After “assay” insert --.--.

In Column 10, Line 53-54, delete “N-acetylneuramic” and insert --N-acetylneuraminic--.

In Column 10, Line 57, delete “N-acetylneuramic” and insert --N-acetylneuraminic--.

In Column 10, Line 61, delete “N-acetylneuramic” and insert --N-acetylneuraminic--.

In Column 10, Line 66, delete “(Beckton” and insert --(Becton--.

In Column 13, Line 22, After “amplifier” insert --.--.

In Column 15, Line 17 (Approx.), delete “N-acetylneuramic” and insert --N-acetylneuraminic--.

In Column 15, Line 21 (Approx.), delete “N-acetylneuramic” and insert --N-acetylneuraminic--.

In Column 15, Lines 24-25, delete “N-acetylneuramic” and insert --N-acetylneuraminic--.

In Column 16, Lines 6-7, delete “N-acetylneuramic” and insert --N-acetylneuraminic--.

Signed and Sealed this
Nineteenth Day of April, 2022

Katherine Kelly Vidal

Katherine Kelly Vidal
*Director of the United States Patent and Trademark Office*

In Column 17, Line 21 (Approx.), delete “octonoate,” and insert --octanoate,--.

In Column 17, Line 62 (Approx.), delete “hemaglutinin” and insert --hemagglutinin--.

In Column 23, Line 2, delete “neurimidase” and insert --neuraminidase--.

In Column 23, Line 42 (Approx.), delete “Syncitial” and insert --Syncytial--.

In Column 23, Line 47 (Approx.), delete “Coronovirus,” and insert --Coronavirus,--.

In Column 26, Line 50, delete “or and” and insert --or/and word--.

In Column 30, Line 2, delete “lanamivir.” and insert --Laninamivir.--.

In Column 31, Line 47, delete “Lanamivir.” and insert --Laninamivir.--.

In Column 32, Line 55, delete “Lanamivir.” and insert --Laninamivir.--.

In the Claims

In Column 37, Claim 1, Line 57, delete “neuramidase” and insert --neuraminidase--.

In Column 38, Claim 15, Line 61, delete “neuramidase” and insert --neuraminidase--.

In Column 39, Claim 19, Line 16 (Approx.), delete “Lanamivir,” and insert --Laninamivir,--.

In Column 40, Claim 40, Line 51 (Approx.), delete “Lanamivir,” and insert --Laninamivir,--.